(12) United States Patent
Wulff et al.

(10) Patent No.: US 9,675,591 B2
(45) Date of Patent: Jun. 13, 2017

(54) METHODS FOR TREATING SEIZURE DISORDERS AND PAIN

(71) Applicant: THE REGENTS OF THE UNIVERSITY OF CALIFORNIA, Oakland, CA (US)

(72) Inventors: Heike Wulff, Davis, CA (US); Nichole Coleman, Davis, CA (US); David Paul Jenkins, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/130,796

(22) Filed: Apr. 15, 2016

(65) Prior Publication Data
US 2016/0228416 A1     Aug. 11, 2016

Related U.S. Application Data

(63) Continuation of application No. PCT/US2014/060759, filed on Oct. 15, 2014.

(60) Provisional application No. 61/904,245, filed on Nov. 14, 2013, provisional application No. 61/891,855, filed on Oct. 16, 2013.

(51) Int. Cl.
*A61K 31/428* (2006.01)
*A61K 45/06* (2006.01)
*C07D 277/82* (2006.01)

(52) U.S. Cl.
CPC ............ *A61K 31/428* (2013.01); *A61K 45/06* (2013.01); *C07D 277/82* (2013.01)

(58) Field of Classification Search
CPC ..... A61K 31/428; A61K 45/06; C07D 277/82
USPC ........................................................ 514/367
See application file for complete search history.

(56) References Cited

U.S. PATENT DOCUMENTS 4,826,860 A    5/1989   Johnson et al.
7,060,723 B2   6/2006   Ehring et al.

FOREIGN PATENT DOCUMENTS

CN        101180276 A     5/2008

OTHER PUBLICATIONS

Sankaranarayanan et al. Mol. Pharmocol., 2009, 75, 281-295.*
Ghasemi et al., "The NMDA receptor complex as a therapeutic target in epilepsy: a review," Epilepsy & Behavior, 2011, vol. 22, pp. 617-640.
Jimonet et al., "Riluzole Series. Synthesis and in Vivo "Antiglutamate" Activity of 6-Substituted-2-benzothiazolamines and 3-Substituted-2-imino-benzothiazolines," J. Med. Chem., 1999, vol. 42, pp. 2828-2843.

* cited by examiner

*Primary Examiner* — Yevegeny Valenrod
(74) *Attorney, Agent, or Firm* — Kilpatrick Townsend & Stockton LLP

(57) ABSTRACT

The present invention provides methods for treating seizure disorders. The method includes administering to a subject in need thereof 2-amino-6-trifluoromethylthio-benzothiazole, or a pharmaceutically acceptable salt thereof. Methods for the treatment of pain are also described.

20 Claims, 19 Drawing Sheets

METHODS FOR TREATING SEIZURE DISORDERS AND PAIN

CROSS-REFERENCES TO RELATED APPLICATIONS

The present application is a continuation of PCT/US2014/060759, filed Oct. 15, 2014, which application claims the benefit of priority to U.S. Provisional Patent Appl. No. 61/891,855, filed Oct. 16, 2013, and U.S. Provisional Patent Appl. No. 61/904,245, filed Nov. 14, 2013, all of which applications are incorporated herein by reference in their entireties.

STATEMENT AS TO RIGHTS TO INVENTIONS MADE UNDER FEDERALLY SPONSORED RESEARCH AND DEVELOPMENT

This invention was made with Government support under Grant Nos. NS072585 and NS079202, awarded by the National Institutes of Health. The Government has certain rights in this invention.

BACKGROUND OF THE INVENTION

Epilepsy, a complex neurological disorder estimated to affect over 50 million people worldwide, is characterized by recurrent spontaneous seizures due to neuronal hyperexcitability and hypersynchronous neuronal firing. Despite the availability of more than 20 antiepileptic drugs (AEDs) about 30% of patients with epilepsy continue to experience seizures or suffer from unacceptable drug side effects such as drowsiness, behavioral changes, liver damage or teratogenicity (Bialer et al., 2013; Bialer et al., 2010). Therefore there remains a substantial unmet need to identify AEDs with novel mechanisms of action that could be used either in monotherapy or integrated into combination regimens to obtain adequate seizure control for presently pharmacoresistant patients.

BRIEF SUMMARY OF THE INVENTION

In a first aspect, the invention provides a method for treating a seizure disorder selected from a limbic seizure, a complex partial seizure, and a chemically-induced seizure. The method includes administering to a subject in need thereof a compound according to formula I, or a pharmaceutically acceptable salt thereof.

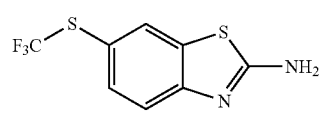

(I)

In a related aspect, the invention provides methods for treating seizure disorders that are susceptible to inhibition of a voltage-gated sodium channel or activation of a small-conductance calcium-activated potassium channel. The methods include administering to a subject in need thereof a compound according to formula I, or a pharmaceutically acceptable salt thereof.

In another aspect, the invention provides methods for treating pain. The methods include administering to a subject in need thereof a compound according to formula I, or a pharmaceutically acceptable salt thereof.

BRIEF DESCRIPTION OF THE DRAWINGS

FIG. 2A shows dose-response curves for seizure protection in the MES test (open squares) and neurological impairment (filled squares) following i.p. administration in mice (n=8 per dose, 2 h time point). ED50 4.8 mg/kg (95% CI, 4.05-5.37), TD50 29.8 mg/kg (95% CI, 25.35-35.98), PI 6.2.

FIG. 2B shows dose-response curves for i.p. administration in rats (n=8 per dose, 1 h time point). ED50 1.6 mg/kg (95% CI, 1.24-1.94), TD50 of 14.33 mg/kg (95% CI, 10.72-17.9), PI 8.9.

FIG. 2C shows dose-response curves for oral administration in rats (n=8 per dose, 4 h time point). ED50 2.33 mg/kg (95% CI, 1.3-3.39), TD50 77.38 mg/kg (95% CI, 62.55-91.01), PI 33.2.

FIG. 3A shows a 6-Hz seizure test in mice: ED50 12.19 mg/kg (95% CI, 8.2-17.45, n=8 per dose). See FIG. 2 for mouse TD50 2 h after i.p. application.

FIG. 3B shows data collected for hippocampal kindled rats: ED50 5.47 mg/kg (95% CI, 2.92-8.92, n=8 per dose).

FIG. 3C shows data collected using a Frings audiogenic seizure (AGS)-susceptible mouse model: $ED_{50}$ 2.15 mg/kg (95% CI 1.52-2.65, n=8 per dose). In all cases, testing was performed 2 h after SKA-19 application.

FIG. 4A shows total SKA-19 plasma concentrations (mean±SD) following i.v. administration of 10 mg/kg in cremophor EL/PBS to male Sprague Daley rats (n=3). The inset shows the same data on a log scale. The data were best fitted as bi-exponential decay and with a quick distribution into tissue followed by elimination ($t_{1/2}$=2.16±0.023 hours).

FIG. 4B shows SKA-19 plasma concentrations following oral gavage application at 10 mg/kg in solution (n=3) or as a methylcellulose suspension (n=3).

FIG. 4C shows plasma concentrations following i.p. application at 10 and 30 mg/kg (n=3).

FIG. 4D shows tissue concentrations 2 hr after i.p. administration of SKA-19 and riluzole at 10 mg/kg (n=3).

FIG. 5E shows sample $Nav_{1.2}$ current traces blocked by 1 µM and 10 µM SKA-19.

FIG. 5F show normalized current vs SKA-19 concentration at −120 mV or −80 mV.

FIG. 5G shows state-dependence: $IC_{50}$ at −70 mV holding potential is 0.86±0.70 µM; $IC_{50}$ at −90 mV holding potential is 7.90±0.01 µM; $IC_{50}$ at −120 mV holding potential is 9.50±1.72 µM.

FIG. 5H shows use-dependence: $IC_{50}$ at 0.1 Hz is 7.90±0.01 µM; $IC_{50}$ at 20 Hz is 0.52±0.23 µM. Data points represent means plus SDs extracted from recordings from at least 3 independent cells.

FIG. 5I shows normalized current vs. pulse number at 1 Hz for SKA-19 at different concentrations.

FIG. 5J shows normalized current vs. pulse number at 20 Hz for SKA-19 at different concentrations.

FIG. 6A shows that SKA-19 concentrations of 1 µM or less have no effect on spontaneous $Ca^{2+}$ oscillations. The arrow indicates addition of SKA-19.

FIG. 6B shows that 4-AP (1 µM, arrow indicates addition) produces an immediate but transient elevation in neuronal intracellular $Ca^{2+}$ followed by increased $Ca^{2+}$ oscillation frequency with lower amplitude. The initial rise and the oscillations are inhibited by SKA-19. SKA-19 was added 10 min before 4-AP.

FIG. 6C shows that picrotoxin (PTX, 10 µM, arrow indicates addition) induces higher amplitude $Ca^{2+}$ oscillations, which are inhibited by SKA-10 (added 10 min before PTX).

FIG. 7A shows that SKA-19 (5 mg/kg administered 2 h prior to formalin injection) significantly decreased the time mice spent licking the affected hindpaw in a 2-min period recorded at 5-min intervals in the formalin pain test (n=8 per group).

FIG. 7B shows the threshold for foot withdrawal in response to a series of calibrated Von Frey fibers in rats 7 days (n=8) after recovery from nerve ligation surgery following administration of SKA-19 (5 mg/kg).

FIG. 8A shows an overlay of representative AP traces recorded before (black) and after (red) perfusion of 1 µM SKA-19 (top) or 25 µM SKA-19 (bottom). Cells were held at −65 mV and a train of APs evoked by a 1-s 150-pA current injection.

FIG. 8B shows an overlay of AP traces recorded in the absence and presence of 10 µM SKA-19 (top), and plot of the number of APs elicited in the presence (red) and absence of SKA-19 in response to stimulating current injections of increasing amplitude (bottom). Data points represent means and SDs for 3 independent neurons.

FIG. 8C shows that SKA-19 enhances the medium afterhyperpolarization (AHP). SKA-19 at a concentration of 10 µM increases the amplitude of the current underlying the medium AHP. Shown on a compressed (top) and expanded time scale (bottom left). Bar graph of normalized $mI_{AHP}$ current amplitude (bottom right). Shown are means and SDs for 3 neurons.

FIG. 8D shows a concentration-response curve for the activation of KCa2.1, KCa2.2, and KCa2.3 recorded in the presence of 250 nM of free intracellular $Ca^{2+}$. See Table 1 for $EC_{50}$ values.

DETAILED DESCRIPTION OF THE INVENTION

I. General

Figure 1:
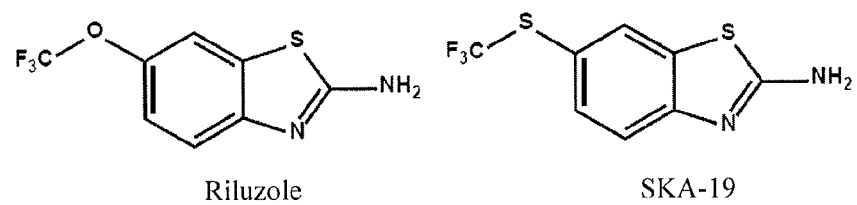
FIG. 1 shows the chemical structures of riluzole (left) and SKA-19 (right).

The present invention is based on the surprising discovery that SKA-19 (6-((trifluoromethyl)thio)benzo[d]thiazol-2-amine), exhibits two modes of action: sodium channel blocking and SK channel (KCa2 channel) activation. The two mechanisms are both anticonvulsant. Without wishing to be bound by any particular theory, it is believed that this dual mechanism contributes to SKA-19's unexpectedly broad anticonvulsant activity as compared to typical sodium channel blockers. The compound also exhibits beneficial analgesic properties.

II. Definitions

As used herein, the term "seizure disorder" refers to a condition characterized by the occurrence of a seizure. A seizure refers to an abnormal electrical discharge in the brain, and signs or symptoms resulting from such an abnormal discharge.

As used herein, the term "partial seizure" refers to a seizure affecting a limited area of the brain. In contrast, a "generalized seizure" is a seizure affecting the entire brain. Symptoms of partial seizures include, but are not limited to, abnormal muscle contraction, staring spells, forced eye movements, abnormal sensations such as numbness and tingling, hallucinations, abdominal pain, nausea, abnormal sweating, rapid heart rate, vision changes, mood changes, and loss of consciousness. Partial seizures are generally classified as "simple" or "complex," based on observed symptoms, analysis of electroencephalographic (EEG) data, or other factors.

As used herein, the term "complex partial seizure" refers to a partial seizure that causes a partial or full loss of consciousness. Complex partial seizures can occur in any area of the brain. Complex partial seizures frequently occur in one of the brain's two temporal lobes. Typical complex partial seizures last for one to two minutes and can be preceded by an "aura" (i.e., a warning sensation such as nausea) that is indicative of an oncoming seizure.

As used herein, the term "simple partial seizure" refers to a partial seizure that does not cause a loss of consciousness. Typical simple partial seizures last 60 seconds or less.

As used herein, the term "limbic seizure" refers to a seizure originating in one of the brain's limbic structures. The limbic system contributes to regulation of the body's unconscious movement and hormonal activity. Limbic structures include, but are not limited to, the thalamus, hypothalamus, cingulate gyrus, amygdala, hippocampus, and basal ganglia.

As used herein, the term "chemically-induced seizure" refers to a seizure in a subject resulting from exposure of the subject to a chemical substance. A chemically-induced seizure can be caused, for example, by a threat agent such as an organophosphate nerve agent or a GABA-antagonist such as the rodenticide tetramethylenedisulfotetramine (TETS).

As used herein, the term "pain" refers to the basic bodily sensation induced by a noxious stimulus and characterized by physical discomfort (e.g., pricking, throbbing, aching, etc.). Pain can include neuropathic pain. Neuropathic pain refers to pain that arises from direct stimulation of nervous tissue and can persist in the absence of the stimulus.

As used herein, the terms "treat," "treating," and "treatment" refer to any indicia of success in the treatment or amelioration of cancer or an injury, pathology, condition, or symptom (e.g., convulsions) related to a seizure disorder or pain; including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "anticonvulsant agent" refers to a substance effective in reducing or eliminating seizures and/or the effects or symptoms of seizures in a subject. Examples of anticonvulsant agents include, but are not limited to, barbiturates (such a phenobarbital), hydantoins (such as ethotoin), succinimides (such as ethosuximide), benzodiazepines (such as clonazepam), carboxamides (such as carbamazepine), GABA analogs (such as gabapentin), pyrrolidines (such as levetiracetam), and fatty acids (such as valproic acid).

As used herein, the term "analgesic agent" refers to a substance effective in reducing or eliminating pain in a subject. Examples of analgesic agents include, but are not limited to, opiates (such as morphine, codeine, and the like); salicylate nonsteroidal anti-inflammatory drugs (such as acetaminophen, aspirin, and the like); nonsalicylate nonsteroidal anti-inflammatory drugs (such as ibuprofen, diclofenac, naproxen, and the like); and calcium channel blocking drugs (such as ziconotide, gabapentin, pregabalin and the like).

As used herein, the term "salt" refers to an acid or base salt of 2-amino-6-trifluoromethylthio-benzothiazole (also known as SKA-19). Illustrative examples of pharmaceutically acceptable salts are mineral acid salts (prepared using hydrochloric acid, hydrobromic acid, phosphoric acid, and the like), organic acid salts (prepared using acetic acid, propionic acid, glutamic acid, citric acid, methanesulfonic acid, maleic acid, and the like), and quaternary ammonium salts (prepared using methyl iodide, ethyl iodide, and the like). It is understood that "pharmaceutically acceptable salts" are non-toxic. Additional information on suitable pharmaceutically acceptable salts can be found in *Remington: The Science & Practice of Pharmacy,* 20th ed., Lippincott Williams & Wilkins, Philadelphia, Pa., 2000, which is incorporated herein by reference.

As used herein, the terms "small-conductance calcium-activated potassium channel," "KCa2 channel," and "SK channel" refer to a tetrameric voltage-insensitive potassium channel having four Shaker-type transmembrane polypeptide subunits. SK channels are activated by low (<1.0 µM) concentrations of internal $Ca^{2+}$ ions. SK channels are sensitive to inhibition by apamin at concentrations ranging from 100 pM to 100 nM. SK channels include KCa2.1, KCa2.2, and KCa2.3, as described, for example by Köhler, et al. (*Science.* 1996, 273 (5282): 1709-14).

As used herein, the term "voltage-gated sodium channel" refers to a sodium channel having a single polypeptide α-subunit with four connected Shaker-type transmembrane domains. Voltage-gated sodium channels generally have one or more auxiliary β-subunits that determine certain aspects of voltage dependence and channel kinetics, as well as cellular localization. Voltage-gated sodium channels are described, for example, by Catterall (*Neuron.* 2000, 26 (1): 13-25). Examples of voltage-gated sodium channels include $Na_v1.1$, $Na_v1.2$, $Na_v1.3$, $Na_v1.4$, $Na_v1.5$, $Na_v1.6$, $Na_v1.7$, $Na_v1.8$, and $Na_v1.9$.

As used herein, a seizure disorder is said to be "susceptible" to activation or inhibition of an ion channel when such activation or inhibition is sufficient to diminish, eliminate, or otherwise alter an indicator (e.g., a symptom or characteristic physiological process) of the disorder. Ion channel activation or inhibition can, for example, be sufficient to diminish a physiological characteristic (e.g., afterdischarge duration) as assessed using a suitable model for a seizure disorder (e.g., a hippocampal kindling model).

III. Methods for Treating Seizure Disorders and Pain

In a first aspect, the invention provides a method for treating a seizure disorder selected from a limbic seizure, a complex partial seizure, and a chemically-induced seizure. The method includes administering to a subject in need thereof a compound according to formula I, or a pharmaceutically acceptable salt thereof.

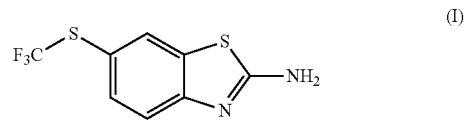 [SMILES: Nc1nc2ccc(SC(F)(F)F)cc2s1]

(I)

The methods of the invention can be used to treat seizure disorders associated with various forms of epilepsy. Epilepsy in its various forms is typically characterized by abnormal electrical discharges in the brain and often manifested by sudden brief episodes of altered or diminished consciousness, involuntary movements, or convulsions. Broadly speaking, forms of epilepsy can be divided into localization-related epilepsies, generalized epilepsies, or epilepsies of unknown localization. The various forms of epilepsy can be classified according to the location or distribution of seizures as determined, for example, by the appearance of the seizures or by electroencephalographic (EEG) analysis, as well as according to cause. There are over 40 different types of epilepsy which include, but are not limited to, absence seizures (petit mal), atonic seizures, benign Rolandic epilepsy, childhood absence epilepsy, clonic seizures, complex partial seizures, frontal lobe epilepsy, febrile seizures, infantile spasms, juvenile myoclonic epilepsy, Lennox-Gastaut syndrome, Landau-Kleffner syndrome, myoclonic seizures, mitochondrial disorders, progressive myoclonic epilepsies, psychogenic seizures, reflex epilepsy, Rasmussen's syndrome, simple partial seizures and epilepsy, secondarily generalized seizures, temporal lobe epilepsy, tonic-clonic seizures (gran mal), tonic seizures, psychomotor seizures, complex partial seizures and epilepsy, limbic epilepsy, partial-onset seizures, generalized-onset seizures, status epilepticus, abdominal epilepsy, akinetic seizures, auto-nomic seizures, massive bilateral myoclonus, catamenial epilepsy, drop seizures, emotional seizures, focal seizures, gelastic seizures, Jacksonian march, Lafora disease, motor seizures, multifocal seizures, neonatal seizures, nocturnal seizures, photosensitive seizures, pseudo seizures, sensory seizures, subtle seizures, Sylvan seizures, withdrawal seizures, and visual reflex seizures, among others.

Complex partial seizures, in particular, account for approximately 40% of all cases in adults, and they are often resistant to available anticonvulsant drugs. Recurrent complex partial seizures are common even when the most effective current therapies are used. See, for example, Arroyo, S. et al., (2002) *Epilepsia* 43(4): 437-444. These attacks induce impairment of consciousness, thereby severely limiting performance of many normal functions (e.g., driving, maintaining employment, etc.). There is no effective prevention or cure for some patients, apart from surgical intervention.

Some embodiments of the invention provide methods for treating seizure disorders, wherein the seizure disorder is a limbic seizure. In some embodiments, the seizure disorder is a complex partial seizure.

In some embodiments, the seizure disorder is a chemically-induced seizure. The methods of the invention can be used to treat chemically-induced seizures caused by a variety of chemical substances. Chemically-induced seizures can be caused, for example, by pentylenetetrazol, bicuculline, penicillin, picrotoxin, β-carbolines, 3-mercapto-propionic acid, hydrazides, allylglycine, strychnine and related alkaloids, γ-hydroxybutyrate, glutamate, aspartate, N-methyl-D-aspartate, quisqualate, kainate, quinolinic acid, monosubstituted guanidino compounds, metals (such as alumina, cobalt, zinc, and iron), neuropeptides (such as opioid peptides, corticotropin releasing factor, somatostatin, and vasopressin), cholinergic agents (acetylcholine, acetylcholinesterase inhibitors, and pilocarpine), tetanus toxin, tetramethylenedisulfotetramine (TETS), flurothyl, folates, and homocysteine.

In some embodiments, the seizure is induced by exposure of the subject to an organophosphate threat agent. Examples of organophosphate threat agents include, but are not limited to, (RS)-ethyl N,N-dimethylphosphoramidocyanidate (tabun); (RS)-propan-2-yl methylphosphonofluoridate (sarin); 3,3-dimethylbutan-2-yl methylphosphonofluoridate (soman); cyclohexyl methylphoshonofluoridate (cyclosarin); S-[2-(diethylamino)ethyl]O-ethyl ethylphosphonothioate (VE); O,O-diethyl S-[2-(diethylamino)ethyl]phosphorothioate (VG); S-[2-(diethylamino)ethyl]O-ethyl methylphosphonothioate (VM); N,N-diethyl-2-(methyl-(2-methylpropoxy)phosphoryl)sulfanylethanamine (VR); ethyl ({2-[bis(propan-2-yl)amino]ethyl}sulfanyl)(methyl)phosphinate (VX); 3-chloro-2-methylpropyl ((chlorofluoromethylene)amino)oxyphosphonofluoridate (Novichok 5); 3-chloro-2-methylbutyl((chlorofluoromethylene)amino) oxyphosphonofluoridate (Novichok 7); 2,2-dichlorovinyl dimethyl phosphate (dichlorvos); diethyl 2-[(dimethoxyphosphorothioyl) sulfanyl]butanedioate (malathion); O,O-diethyl O-(4-nitrophenyl) phosphorothioate (parathion); and O,O-dimethyl O-(4-nitrophenyl) phosphorothioate (methyl parathion).

In some embodiments, the subject is known to be susceptible to the seizure disorder. In some embodiments, the subject has been diagnosed with a condition associated with limbic seizures, complex partial seizures, or limbic and complex partial seizures.

In a related aspect, the invention provides a method for treating seizure disorders that are susceptible to inhibition of a voltage-gated sodium channel or activation of a small-conductance calcium-activated potassium channel. The methods include administering to a subject in need thereof a compound according to formula I, or a pharmaceutically acceptable salt thereof. In some embodiments, the seizure disorder is susceptible to inhibition of a voltage-gated sodium channel. In some embodiments, the seizure disorder is susceptible to activation of a small-conductance calcium-activated potassium channel. In some embodiments, the seizure disorder is susceptible to inhibition of a voltage-gated sodium channel and activation of a small-conductance calcium-activated potassium channel. In some embodiments, the voltage-gated sodium channel is selected from Nav1.1, Nav1.2, and Nav 1.6. In some embodiments, the small-conductance calcium-activated potassium channel is selected from KCa2.1, KCa2.2, and KCa2.3

In some embodiments, administration of the compound is sufficient to treat pain in the subject.

In another aspect, the invention provides a method for treating pain. The method includes administering to a subject in need thereof a compound according to formula I, or a pharmaceutically acceptable salt thereof.

The methods of the invention can be used to treat pain associated with any noxious stimulus and causing physical discomfort. In certain embodiments, the methods can be used to treat neuropathic pain. The sensations that characterize neuropathic pain vary, and multiple sensations often occur simultaneously. Neuropathic pain can manifest as burning, gnawing, aching, shooting, and other sensations. In certain instances, damaged nerve fibers send incorrect signals to other pain centers. The impact of nerve fiber injury includes a change in nerve function both at the site of injury and areas around the injury. Chronic neuropathic pain can frequently appear to have no obvious cause. However, common causes can include alcoholism, amputation, back, leg and hip problems, chemotherapy, diabetes, facial nerve problems, HIV infection or AIDS, multiple sclerosis, shingles, and spine surgery. One example of neuropathic pain is phantom limb syndrome, which occurs when an arm or leg has been removed because of illness or injury, but the brain still receives signals from the nerves that originally carried impulses from the missing limb.

IV. Formulation and Administration

SKA-19 can be administered at any suitable dose in the methods of the invention. In general, SKA-19 is administered at a dose ranging from about 0.1 milligrams to about 1000 milligrams per kilogram of a subject's body weight (i.e., about 0.1-1000 mg/kg). The dose of SKA-19 can be, for example, about 0.1-1000 mg/kg, or about 1-500 mg/kg, or about 25-250 mg/kg, or about 50-100 mg/kg. The dose of SKA-19 can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The dose of SKA-19 can be administered at a dose below about 1, below about 2, below about 3, below about 4, below about 5, below about 10, below about 15, below about 20, below about 25, below about 30, below about 35, below about 40, below about 45, below about 50, below about 55, below about 60, below about 65, below about 70, below about 75, below about 85, below about 90, below about 95, below about 100, below about 150, below about 200, below about 250, below about 300, below about 350, below about 400, below about 450, below about 500, below about 550, below about 600, below about 650, below about 700, below about 750, below about 800, below about 850, below about 900, below about 950, or below about 1000 mg/kg. In some embodiments, SKA-19 is administered at a dose below 200 mg of compound per kg of the subject's body weight (200 mg/kg). In some embodiments, SKA-19 is administered at a dose below 100 mg/kg. In some embodiments, SKA-19 is administered at a dose below 50 mg/kg. In some embodiments, SKA-19 is administered at a dose below 20 mg/kg.

The dosages can be varied depending upon the requirements of the patient, the severity of the disorder being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the seizure disorder.

Administration of SKA-19 can be conducted for a period of time which will vary depending upon the nature of the particular disorder, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the disorder. The dosage of the SKA-19 can either be increased in the event the patient does not respond significantly to a particular dosage level, or the dose can be decreased if an alleviation of the symptoms of the disorder is observed, or if the disorder has been ablated, or if unacceptable side effects are seen with a particular dosage.

A therapeutically effective amount of SKA-19 can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the disorder goes into remission or generally improves, the dosage may be maintained or kept at lower than maximum amount. If the seizure disorder relapses, the first dosage regimen can be resumed until an improvement is seen, and the second dosing regimen can be implemented again. This cycle can be repeated multiple times as necessary.

In some embodiments, SKA-19 is administered to the subject before the seizure onset. In some embodiments, the compound is administered to the subject at least 10 minutes before the seizure onset. In some embodiments, the compound is administered to the subject at least one hour before the seizure onset. In some embodiments, the compound is administered to the subject at least four hours before the seizure onset. In certain instances, persons afflicted with seizure disorders are known to experience warning sensations, often referred to as auras, preceding the onset of a seizure. An aura can occur immediately before, a few minutes before, or hours before a seizure begins. An aura can include one or more sensations such as, but not limited to, nausea, changes in vision (e.g., dark spots or bright lights in the field of vision), auditory and olfactory hallucinations, numbness, tingling, and anxiety. In some embodiments, SKA-19 is administered to the subject while the subject is experiencing an aura. In some embodiments, the compound is administered to the subject during the seizure.

In a related aspect, the invention provides pharmaceutical compositions for the administration of SKA-19. The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

The pharmaceutical compositions can be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Aqueous suspensions contain the active materials in admixture with excipients suitable for the manufacture of aqueous suspensions. Such excipients include, but are not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the active ingredient in a vegetable oil, for example, arachis oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules (suitable for preparation of an aqueous suspension by the addition of water) can contain the active ingredient in admixture with a dispersing agent, wetting agent, suspending agent, or combinations thereof. Additional excipients can also be present.

The pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Pharmaceutical compositions containing SKA-19 can also be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semipermeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Transdermal delivery of SKA-19 can be accomplished by means of iontophoretic patches and the like. The compound can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

In some embodiments, SKA-19 is administered via intraperitoneal injection. In some embodiments, the compound is administered orally.

In some embodiments, the method further includes administering to the subject one or more agents selected from the group consisting of anticonvulsant agents and analgesic agents.

Any suitable anticonvulsant agent can be used in the methods of the invention. Examples of anticonvulsant agents include, but are not limited to, acetazolamide, brivaracetam, carbamazepine, clonazepam, diazepam, divalproex, ethosuximide, ethotoin, felbamate, gabapentin, lamotrigine, levetiracetam, mephenytoin, mephobarbital, methsuximide, oxcarbazepin, paramethadione, phenacemide, pheneturide, phenobarbital, phenytoin, pregabalin, primidone, seletracetam, stiripentol, topiramate, trimethadione, valproic acid, and vigabatrin.

Any suitable analgesic agent can be used in the methods of the invention. Examples of analgesic agents include, but are not limited to: morphine, morphine sulfate, codeine, codeine phosphate, codeine sulfate, hydrocodone bitartrate, hydromorphone hydrochloride, levorphanol tartrate, oxycodone hydrochloride, oxymorphone hydrochloride, naloxone hydrochloride, naltrexone hydrochloride, alfentanil hydrochloride, buprenorphine hydrochloride, butorphanol tartrate, dezocine, fentanyl citrate, meperidine hydrochloride, methadone hydrochloride, nalbuphine hydrochloride, pentazocine, propoxyphene hydrochloride, propoxyphene napsylate, sufentanil, tramadol hydrochloride, acetaminophen, aspirin, bromfenac sodium, diclofenac sodium diflunisal, etodolac, fenoprofen calcium, flurbiprofen, ibuprofen, indomethacin, ketoprofen, meclofenamate sodium, mefenamic acid, nabumetone, naproxen, naproxen sodium, oxyphenbutazone, phenylbutazone, piroxicam, sulindac, tolmetin sodium, auranofin, aurothioglucose, allopurinol, chochicine, sulfinpyrazone, ziconotide, gabapentin, and pregabalin.

V. Examples

Material and Methods

Drugs.

SKA-19 (2-amino-6-trifluoromethylthio-benzothiazole, CAS 326-45-4) and riluzole (CAS 1744-22-5) were purchased from Oakwood Products (West Columbia, S.C.) and recrystallized for the experiments. $^1$H and $^{13}$C nuclear magnetic resonance were used to confirm identity and purity.

Seizure Assays.

SKA-19 was tested under the auspices of the National Institutes of Health's Anticonvulsant Screening Program (ASP). Experiments were performed in male albino CF (Carworth Farms) No. 1 mice or Sprague-Dawley rats according to the established protocols of the ASP (White et al., 2002). SKA-19 was suspended in 0.5% methylcellulose and administered in a volume that permits accuracy of dosage without excessively contributing to total body fluid (0.01 ml/g body weight for mice and 0.04 ml/10 g body weight for rats).

Maximal Electroshock Test.

Animals received an electrical stimulus of 0.2 s duration (50 mA in mice and 150 mA in rat at 60 Hz) delivered via corneal electrodes primed with an electrolyte solution containing 0.5% tetracaine. Animals were restrained by hand and released immediately after stimulation to permit observation of the seizure throughout its entire course. In the initial screens to identify anticonvulsant activity mice were tested at 30 minutes and 4 hours following doses of 3, 10, 30, 100 and 300 mg/kg of SKA-19 and rats tested at time intervals between 0.25 and 4 hours following a standard oral dose of 30 mg/kg. In the subsequent, more quantitative tests at least four doses of SKA-19 (n=8 per dose) were tested at the previously determined time of peak effect (TPE). Abolition of hindlimb tonic extension indicates the test compound's ability to inhibit MES-induced seizure spread. Tonic extension is considered abolished if the hind limbs are not fully extended at 180° with the body.

MES assays were performed at the Department of Neurology at the University of California with CF-1 mice. This study was approved by the University of California, Davis, Animal Use and Care Committee and conducted in accordance with the guidelines of Animal Use and Care of the National Institutes of Health and the University of California. For these assays, stock solutions of SKA-19 (5 mg/ml) were prepared in 5% CremophorEL (Sigma-Aldrich, St. Louis, Mo., USA) and 95% saline, diluted further with saline, and SKA-19 was administered i.p. in a volume of 10 ml/kg body weight. Animals were subjected to a 0.2-s, 60-Hz electrical stimulus through corneal electrodes (5 mm diameter stainless steel balls). The electroshock unit was adjusted to deliver a constant current of 50 mA. Immediately before stimulation, the corneal electrodes were wetted with saline to provide good electrical contact. Animals failing to show tonic hindlimb extension were scored as protected (Kokate et al., 1994).

Subcutaneous Metrazol Seizure Test (s.c. MET).

A dose of subcutaneous pentylenetetrazole (Metrazole, MET) which induces convulsions in 97% of animals (CD97: 85 mg/kg mice or 56.4 mg/kg rats) was injected into a loose fold of skin at the neck. Animals were placed in isolation cages and observed for 30 min for the occurrence of clonic spasms persisting for at least 5 s. Test compound was administered i.p. or through oral dosing at various times before scMET and animals not exhibiting seizures were considered protected.

6-Hz Psychomotor Seizure Test.

Seizures characterized by a minimal clonic phase followed by stereotyped automatistic behaviors (jaw chomping and whisker movement) were induced in mice by a low frequency (6 Hz), long-duration (3 s) stimulus. These seizures resemble automatistic behavior in patients with complex partial seizures. At varying times (0.25, 0.5, 1, 2, and 4 h) after drug treatment, individual mice (four at each time point) were challenged with sufficient current (32 or 44 mA at 6 Hz for 3 s) delivered through corneal electrodes to elicit a psychomotor seizure. Animals not displaying this behavior are considered protected.

Hippocampal Kindled Seizures.

Bipolar electrodes were surgically implanted into the hippocampus of anesthetized rats, which were allowed to recover for one week. One week after the surgery, the rats were stimulated with suprathreshold trains of 200 µAmps for 10 sec, 50 Hz, every 30 min for 6 hours (12 stimulations per day) on alternate days (4 to 5 stimulus days) until they were fully kindled. One week later the effect of a single i.p. dose of test compound was assessed on behavioral seizure score (BSS) and afterdischarge duration (ADD). An initial group of kindled rats (n=6-8) were tested at 15, 45, 75, 105, 135, 165, and 195 min after drug administration. Results obtained at the various time points were compared with the last control stimulus delivered 15 minutes prior to drug administration. Thus, each animal serves as its own control. The BSS's were scored according to the following criteria: Stage 1—mouth and facial clonus; Stage 2—stage 1 plus head nodding; Stage 3—stage 2 plus forelimb clonus; Stage 4—stage 3 plus rearing; Stage 5—stage 4 plus repeated rearing and falling. The afterdischarge threshold (ADT) is measured in the kindled rat. Since the initial SKA-19 treatment (30 mg/kg) was observed to completely abolish seizures and afterdischarge, a dose-response study was initiated. The BSS and ADD for each dose were averaged at the TPE, the S.E.M. calculated, and the significance of the difference compared to control values determined. (Significant differences in BSS from control and treated groups are determined by the non-parametric Mann-Whitney U test). The ability of SKA-19 to reduce seizure severity was quantitated by varying the dose between 0 and 100%, noting those animals having a BSS of 3 or less in the group, and calculating an $ED_{50}$ by probit analysis.

Frings Audiogenic Seizure-Susceptible Mice.

Frings audiogenic seizure (AGS)-susceptible mice are genetically susceptible to sound-induced seizures (Frings et al., 1953). A colony of AGS mice is maintained by the ASP at the University of Utah. Groups of 8 female mice (weighing 18-25 g) were treated i.p. with increasing doses of SKA-19. At the TPE in the MES test, mice were exposed to a sound stimulus of 110 decibels (11 KHz) delivered for 20 s. Mice were observed for the presence or absence of hindlimb tonic extension.

Infusion of Metrazol (i.v. Met) Test.

The i.v. Met test provides a measure of a test substance's ability to raise or lower seizure threshold. Two doses of the test compound are usually employed in this test, the MES $ED_{50}$ and the $TD_{50}$ determined following i.p. quantification testing in mice. SKA-19 was accordingly tested at 5 and 30 mg/kg. Randomly selected mice (n=30) were injected i.p. 2 minutes apart with either the vehicle or the two test drug doses. At the previously determined TPE, 0.5% heparinized Metrazol solution was infused at a constant rate of 0.34 ml/min into a lateral tail vein. The time in seconds from the start of the infusion to the appearance of the "first twitch" and the onset of sustained clonus is recorded. The times to each endpoint are converted to mg/kg of Metrazol for each mouse as follows: mg/kg Met=Infusion time (T)×Rate of infusion (ml/min)×mg Met/ml×1000 g/60 sec×Weight (W) of animal in g=T×0.34×5×1000=28.33×T=mg/kg of Metrazol 60×W W. The mean and S.E. for each of the 3 groups and the significance of the difference between the test groups and the control are calculated. An increase in mg/kg to first twitch or to clonus indicates the test substance increases seizure threshold; whereas a decrease indicates that the test substance decreases seizure threshold and is a proconvulsant.

Acute Toxicity.

Abnormal neurological status in mice following SKA-19 administration was evaluated with the rotorod test. When a normal mouse is placed on a rod 1 inch in diameter that rotates at a speed of 6 rpm, the mouse can maintain equilibrium for a long time. Inability of the mouse to stay on the rotating rod in three trials for 1 min is taken as an indication of motor impairment. For $TD_{50}$ curves, motor toxicity was evaluated using a modification of the horizontal screen test as previously described (Kokate et al., 1994). Mice were placed on a horizontally oriented grid (consisting of parallel 1.5-mm diameter rods situated 1 cm apart), and the grid was inverted. Animals that fell from the grid within 10 s were scored as impaired.

Abnormal neurological status in rats was evaluated by the positional sense test, the muscle tone test, and the gait and stance test. Inability of the rat to perform normally in at least two of these tests is taken as an indication of some neurological deficit.

Statistical Analysis.

$ED_{50}$s and $TD_{50}$s were calculated at the ASP by a FORTRAN probit analysis program, which provides the 95% confidence intervals, the slope of the regression lines, and the standard error of the slopes. For the 6-Hz experiments a similar log-probit analysis was performed with the Litchfield and Wilcoxon method (PHARM/PCS Version 4.2; Micro-Computer Specialists, Philadelphia, Pa.) to calculate $ED_{50}$ and $TD_{50}$ values and their corresponding 95% confidence intervals.

Formalin Pain Assay.

SKA-19 was administered at a dose of 5 mg/kg to CF-1 male mice. At the previously determined time of peak anticonvulsant effect 0.5% formalin was injected sub-dermally into the plantar surface of the right hind foot. For each animal the amount of time (s) spent licking the affected hind paw in a two minute period was recorded at 5 minute intervals and continued for 45 minutes through both the acute and inflammatory phase.

Pain Assay—Partial Ligation of the Sciatic Nerve.

Rats were anesthetized with sodium pentobarbital, the upper thigh shaved and wiped off with ethanol and betadine. A small incision was made in the skin and the underlying muscle separated to expose the sciatic nerve. Approximately ⅓ to ½ of the nerve was tied off by passing a needle (7.0) and nylon suture through the nerve. The muscle and skin incision were afterwards closed off and the animals kept warm until they had recovered from the anesthesia. This procedure was performed on the right side (ipsilateral) while a sham surgery exposing but not ligating the nerve was performed on the left hind leg (contralateral). After 7 days of recovery animals were tested for the development of mechanical allodynia (abnormal response to a non-noxious stimulus) by putting them in a bottomless plexiglass box placed on a wire mesh (¼") platform. After 30-60 min of acclimatization a baseline mechanical sensitivity was determined by applying a series of calibrated Von Frey fibers perpendicularly to the plantar surface of each hind paw and holding it there for about 6 s with enough force to slightly bend the fiber. After a positive response (withdrawal of the foot) was noted a weaker fiber was applied. This was repeated until a 50% threshold for withdrawal could be determined. The allodynic threshold was then redetermined after i.p. application of SKA-19 at 5 mg/kg at the time-to-peak effect determined in the acute seizure models.

Pharmacokinetics.

Nine- to 11-week-old male Sprague-Dawley rats were purchased from Charles River Laboratories (Wilmington, Mass.) and housed in microisolator cages with rodent chow and autoclaved water ad libitum. All experiments were in accordance with National Institutes of Health guidelines and approved by the University of California, Davis, Institutional Animal Care and Use Committee.

For intravenous application, SKA-19 was dissolved at 5 mg/mL in a mixture of 10% CremophorEL (Sigma-Aldrich, St. Louis, Mo., USA) and 90% phosphate-buffered saline and then injected at 10 mg/kg into the tail vein of Sprague-Dawley rats. At various time points after the injection, ~100 to 200 µL of blood was collected from a tail nick into EDTA blood sample collection tubes. Plasma was separated by centrifugation and stored at −80° C. pending analysis. For intraperitoneal application SKA-19 was dissolved in Miglyol 812 neutral oil (caprylic/capric triglyceride; Trade name Neobee M5, Spectrum Chemicals, Gardena, Calif., USA) at 2 mg/mL and injected intraperitoneally at 10 and 30 mg/kg. After determining that SKA-19 plasma concentrations peaked 2 h after i.p. application, a group of 3 rats was subjected to cardiac puncture under deep isoflurane anesthesia and then sacrificed before removing brain, heart, liver, spleen and fat. Tissue samples were homogenized in 1 ml of $H_2O$ with a Brinkman Kinematica PT 1600E homogenizer and the protein precipitated with 1 ml of acetonitrile. The samples were then centrifuged at 3000 rpm and supernatants concentrated to 1 ml. Plasma and homogenized tissue samples were purified using $C_{18}$ solid phase extraction cartridges. Eluted fractions corresponding to SKA-19 were dried under nitrogen and reconstituted in acetonitrile. LC/MS analysis was performed with a Waters Acquity UPLC (Waters New York, USA) equipped with a Acquity UPLC BEH 1.7 µm RP-18 column (Waters New York, USA) interfaced to a TSQ Quantum Access Max mass spectrometer (MS) (ThermoFisher Scientific, Waltham, Mass., USA). The mobile phase consisted of acetonitrile and water, both containing 0.1% formic acid. With a flow rate of 0.25 mL/min, the gradient was ramped from 95% water to 95% ACN in 6 minutes with a retention time (rt) of 3 minutes. Using electrospray ionization MS and selective reaction monitoring (SRM) (capillary temperature 350° C., capillary voltage 4000 V, collision energy −26 eV, positive ion mode), SKA-19 was quantified by its base peak of 182.9 m/z ($C_7H_7N_2S_2^{\cdot+}$ fragment) and its concentration was calculated with a 9-point calibration curve from 50 nmol/L to 10 µmol/L. The percentage of plasma protein binding for SKA-19 was determined by ultrafiltration. Rat plasma was spiked with SKA-19 in 1% dimethylsulfoxide and the sample loaded onto a Microcon YM-100 Centrifugal Filter (Millipore Corp., Bedford, Mass., USA) and centrifuged at 14,000 g for 15 minutes at room temperature. The centrifugate (=free SKA-19) was directly analyzed for SKA-19 by UPLC-MS. The retentate was collected by inverting the filter into an Eppendorf tube and spinning at 14,000 g for 15 minutes. The retentate then underwent sample preparation as per the above-described procedure for determining total SKA-19 concentration in plasma. The plasma protein binding of SKA-19 was found to be 89±0.5% (n=3) and the unbound (=free) fraction 9.0±0.4%.

Primary Cultures of Hippocampal Neurons.

Animals were treated humanely and with regard for alleviation of suffering according to protocols approved by the Institutional Animal Care and Use Committee of the University of California, Davis. Hippocampal neuron cultures were dissociated from hippocampi dissected from C57Bl/6J mouse pups at postnatal day 0-1 and maintained in Neurobasal complete medium (Neurobasal medium supplemented with NS21, 0.5 mM L-glutamine, HEPES) with 5% fetal bovine serum. For $Ca^{2+}$ imaging studies using FLIPR, dissociated hippocampal cells were plated onto poly-L-lysine coated clear-bottom, black wall, 96-well imaging plate (BD, Franklin Lakes, N.J., USA) at a density of $0.8 \times 10^5$/well. The medium was changed twice a week by replacing half the volume of culture medium in the well with serum-free Neurobasal complete medium. The neurons were maintained at 37° C. with 5% $CO_2$ and 95% humidity.

Measurement of Synchronous Intracellular $Ca^{2+}$ Oscillations.

Hippocampal neurons 14-17 DIV were used for simultaneous measurements of intracellular $Ca^{2+}$ transients in all wells of a 96-well plate as described previously (Cao et al., 2012). After aspiration, the cells were incubated with 4 µM Fluo-4 in Locke's buffer containing 0.5 mg/ml bovine serum albumin for 1 h at 37° C. The plates were then transferred to the FLIPR (Molecular Devices, Sunnyvale, Calif., USA) cell plate stage. After 4 min of baseline recordings, $Ca^{2+}$ signals were then recorded for 10 min in the presence or absence of SKA-19 followed by addition of the $Ca^{2+}$ enhancing agents 4-AP or PTX, and the intracellular $Ca^{2+}$ concentration ($[Ca^{2+}]_i$) was monitored for an additional 30 min. $Ca^{2+}$-enhancing agents triggered an immediate rise in $[Ca^{2+}]_i$ that was quantified by determining the area under the curve of the Fluo-4 arbitrary fluorescence units for a duration of 5 min following agent addition.

Slice Recordings.

Brain slice preparation was approved by the University of California, Irvine, Institutional Animal Care and Use Committee. Male C57BL/6 J mice (postnatal day 23) were anesthetized with halothane, decapitated, and brains transferred to an ice-cold, sucrose artificial cerebral spinal fluid (ACSF; Sigma-Aldrich). Hippocampal slices (300 μm) were prepared using a Leica VT1200S vibrating blade microtome (Leica Microsystems Inc., Buffalo Grove, Ill.). Slices were incubated at 33° C. in oxygenated (95% $O_2$, 5% $CO_2$) standard ACSF containing the following (mM) for at least 1 h before recordings: 126 NaCl, 2.5 KCl, 1.25 $NaHPO_4$, 1.2 $MgSO_4$, 10 glucose, 1.2 $CaCl_2$, and 26 $NaHCO_3$. Slices were submerged and continuously perfused at 2 ml/min with oxygenated ACSF at 33° C. during the current-clamp experiments. Voltage-clamp experiments were performed in the same ACSF but with 1 mM tetraethylammonium chloride (Sigma-Aldrich) and 0.5 μM tetrodotoxin (Sigma-Aldrich) added. Pyramidal CA1 neurons were visualized and identified with an upright microscope (Zeiss Axioskop Plus; Zeiss Jena, Germany) with infrared differential interference contrast optics. Recording pipettes (2-5 MΩ) were filled with intracellular solution containing (in mM): 126 K-gluconate; 4 KCl; 10 HEPES; 2 Mg-adenosine triphosphate; 0.3 Tris-guanosine triphosphate; 10 phosphocreatine, pH 7.20, 270-290 mOsm. In the current-clamp mode, depolarizing current pulses were applied from a membrane potential of −65 mV to evoke tonic firing activity. In the voltage-clamp mode, neurons were held at −55 mV and KCa currents elicited by 50-ms voltage steps to 10 mV, applied every 10 s. SKA-19 or NS309 were perfused for 10 min into the bath to allow for equilibrium. Recordings were performed in the whole-cell mode using a MultiClamp 700B amplifier (Molecular Devices), digitized at 4 kHz and sampled at 20 kHz with a Digidata 1322A digitizer (Molecular Devices). Data were acquired and analyzed with pClamp 10.2 software (Molecular Devices).

Voltage-Clamp Experiments.

All experiments were conducted at room temperature (22-24° C.) with an EPC-10 amplifier and Pulse software (HEKA, Lambrecht/Pfalz, Germany) in the whole-cell mode of the patch-clamp technique. Human embryonic kidney (HEK)-293 cell lines stably expressing $hNa_v1.1$, $hNa_v1.5$, $hNa_v1.7$ channels (generously provided by Dr. Christopher Lossin, University of California Davis), $hNa_v1.4$ (Frank Lehmann-Horn, University of Ulm), or $hK_v2.1$ channels (James Trimmer, University of California Davis) were bathed in extracellular solution containing (in mM): 160 NaCl; 4.5 KCl; 1 $MgCl_2$; 2 $CaCl_2$; 10 HEPES [pH was adjusted to 7.4 using NaOH (310 mOsm)]. Pipettes were filled with intracellular solution containing (in mM): 145 KF; 2 $MgCl_2$; 10 ethylene glycol tetraacetic acid; 10 HEPES (pH adjusted to 7.2 with KOH; 300 mOsm). Neuroblastoma N1E-115 cells (ATCC, Manassa, Va., USA) expressing $Na_v1.2$ were patched with a CsF internal solution consisting of (in mM): 10 NaF; 110 CsF; 20 CsCl; 2 ethylene glycol tetraacetic acid; 10 HEPES (CsOH to pH 7.35; 300 mOsm). All pipette tip resistances were 2-4 MΩ. Series resistances of 3-10 MΩ were compensated 40-80%. All cells were voltage-clamped to a holding potential of −90 mV unless otherwise specified. The sampling frequency was 5 kHz. $Na^+$ currents were elicited by 30-ms pulse to 0 mV from −90 mV applied every 10 s. $K_v2.1$ currents were elicited by 200-ms voltage steps from −90 to 40 mV applied every 10 s.

HEK-293 or COS-7 cells stably expressing hKCa2.1, rKCa2.2, and hKCa2.3 have been described previously (Sankaranarayanan et al., 2009). Cells were held at −80 mV and KCa currents elicited by dialysis with a $K^+$ aspartate based internal containing 250 nM free $Ca^{2+}$ (pH 7.2, 290 mOsm, pipette resistance 1.5 MΩ). To reduce currents from native chloride channels, $Na^+$ aspartate Ringer was used as an external solution. KCa2 currents were recorded with 200-ms voltage ramps from −120 to +40 mV applied every 10 s, and the fold increase of slope conductance at −80 mV by drug was taken as a measure of channel activation. Data analysis, fitting, and plotting were performed with IGOR-Pro (Wavemetrics, Lake Oswego, Oreg., USA) and Origin 9.0 (OriginLab, Northampton, Mass., USA).

Electrophysiology-Measurement of Synchronous Intracellular $Ca^{2+}$ Oscillations.

Hippocampal neurons between 13-17 days in vitro (DIV) were used to investigate how $Ca^{2+}$ enhancing agent alters synchronous $Ca^{2+}$ oscillations that normally occur in healthy neurons at this developmental stage. This method permits simultaneous measurements of intracellular $Ca^{2+}$ transients in all wells of a 96-well plate as described previously (Cao et al., 2012). Baseline recordings were acquired in Locke's buffer (8.6 mM HEPES, 5.6 mM KCl, 154 mM NaCl, 5.6 mM glucose, 1.0 mM $MgCl_2$, 2.3 mM $CaCl_2$, and 0.0001 mM glycine, pH 7.4) for 10 min in presence or absence of SKA-19 followed by addition of the $Ca^{2+}$ enhancing agents 4-aminopyridine (4-AP) or picrotoxin using a programmable 96-channel pipetting robotic system, and the intracellular $Ca^{2+}$ concentration ($[Ca^{2+}]_i$) was monitored for an additional 30 min. Unless otherwise indicated, pharmacological interventions were introduced 10 min prior to $Ca^{2+}$ enhancing agent. Ca enhancing agent triggered an immediate rise in $[Ca^{2+}]_i$ that was quantified by determining the area under the curve (AUC) of the Fluo-4 arbitrary fluorescence units for a duration of 5 min following $Ca^{2+}$ enhancing agent addition. $Ca^{2+}$ enhancing agent also altered the frequency and amplitude of neuronal synchronous $Ca^{2+}$ oscillations, which were analyzed during the 10 min period after addition of $Ca^{2+}$ enhancing agent for 15 mM.

Results

In general, there are currently three approaches for identifying new AEDs (Bialer et al., 2010). The first approach, which is intellectually most satisfying, is a mechanism based approach in which drugs are specifically developed for a molecular target validated through human mutations and/or genetic manipulations in rodents. An example is the ongoing search for potent and selective Kv7.2/7.3 (KCNQ2/3) activators like ICA-27243, ICA-105665 or other retibagine related compounds (Dalby-Brown et al., 2013; Rigdon, 2009; Roeloffs et al., 2008). These chemistry programs were initiated based on the observation that loss-of function mutations in Kv7.2 (KCNQ2) have been associated with benign familial neonatal convulsions (BFNC), a rare hereditary form of human epilepsy (Biervert et al., 1998). The second approach is to design follow-up compounds to existing AEDs with more favorable side-effect or pharmacokinetic profiles such as eslicarbazepine as a second generation drug to oxcarbazepine and a third generation drug to carbamazepine. The third approach, which has been pursued by the NIH Anticonvulsant Screening Program (ASP) since 1975, is empirical and uses rodent models of convulsions. We here used a serendipitous combination of all three approaches to identify SKA-19 (2-amino-6-trifluoromethyl-thio-benzothiazole), a thioanalog of the neuroproctant riluzole, as a potent, novel anticonvulsant (FIG. 1.).

SKA-19 (2-amino-6-trifluoromethylthio-benzothiazole) has now been found to be a surprisingly potent, orally active anticonvulsant. The compound demonstrates efficacy in seizure types that are difficult to treat. Mechanism of action studies show that SKA-19 suppresses $Ca^{2+}$ oscillations in cultured hippocampal neurons induced by picrotoxin and 4-aminopyridine (4-AP) and inhibits voltage-gated $Na^+$ channels as well as activates KCa2 channels at low micromolar concentrations. Furthermore, SKA-19 reduced the acute pain response in the formalin pain model and sciatic nerve ligation model. Without wishing to be bound by any particular theory, we propose that the dual mechanism of action of SKA-19—combining KCa2 channel activating activity and $Na_v$ channel blocking activity—contributes to its broad-spectrum anticonvulsant and analgesic effects.

SKA-19 is Active in the MES Seizure Test.

SKA-19 was evaluated for anti-ictal activity in the initial qualitative screens of the ASP which are used for routine identification of potential novel anticonvulsants. These so-called "Identification" tests evaluate a compound at increasing doses in the maximal electroshock seizure (MES) and the subcutaneous Metrazole (scMET) model combined with an initial assessment of toxicity. The MES test is a model for generalized tonic-clonic seizures and provides an indication of a compound's ability to prevent seizure spread, while the scMET test identifies compounds able to raise the threshold for seizures induced by the $GABA_A$ receptor antagonist pentylenetetrazole. SKA-19 fully protected mice in the MES model following i.p. administration at 10, 30 and 100 mg/kg and exhibited partial protection at 3 mg/kg. However, it did not provide any protection in the scMET test at 30 and 100 mg/kg, while one animal treated with 300 mg/kg died in the scMET test without exhibiting a seizure. Preliminary toxicity testing for neurological deficits revealed no impairment of the ability of mice to stay on the rotorod at 0.5 and 4 hours after doses of 3, 10 and 30 mg/kg, but showed inability to clasp the rotorod at 100 mg/kg and sedation or death at 300 mg/kg. Following oral application at 30 mg/kg SKA-19 also fully protected rats from MES induced seizures at all tested time points (0.25, 0.5, 1, 2 and 4 h) without inducing neurotoxicity (n=4).

Figure 2A:
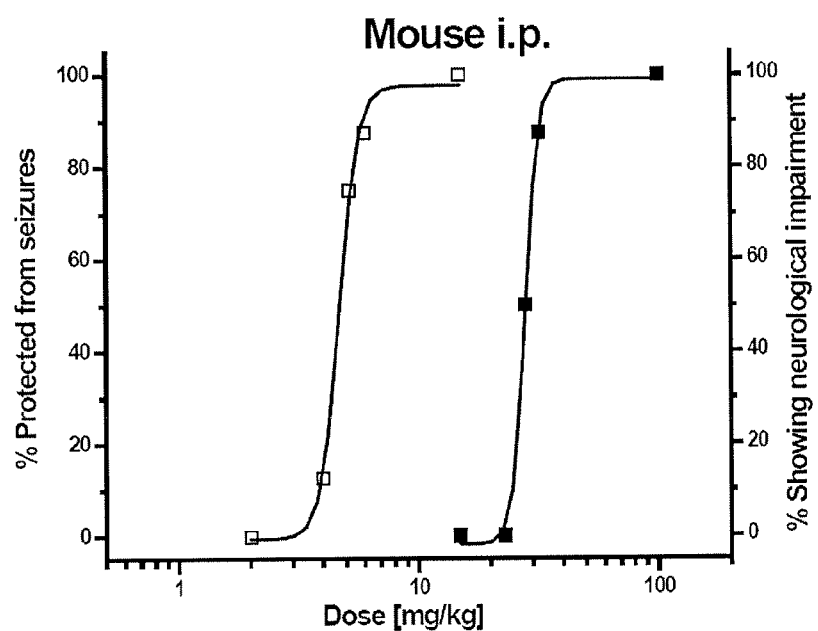
FIG. 2A-FIG. 2C show that SKA-19 protects mice and rats in the maximum electroshock (MES)-induced seizure model.
Figure 2B:
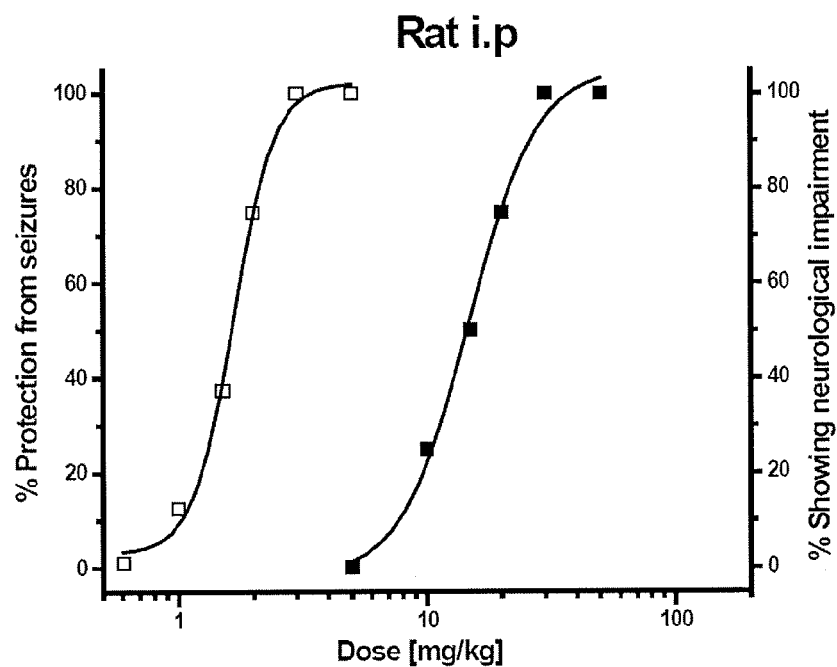
Figure 2C:
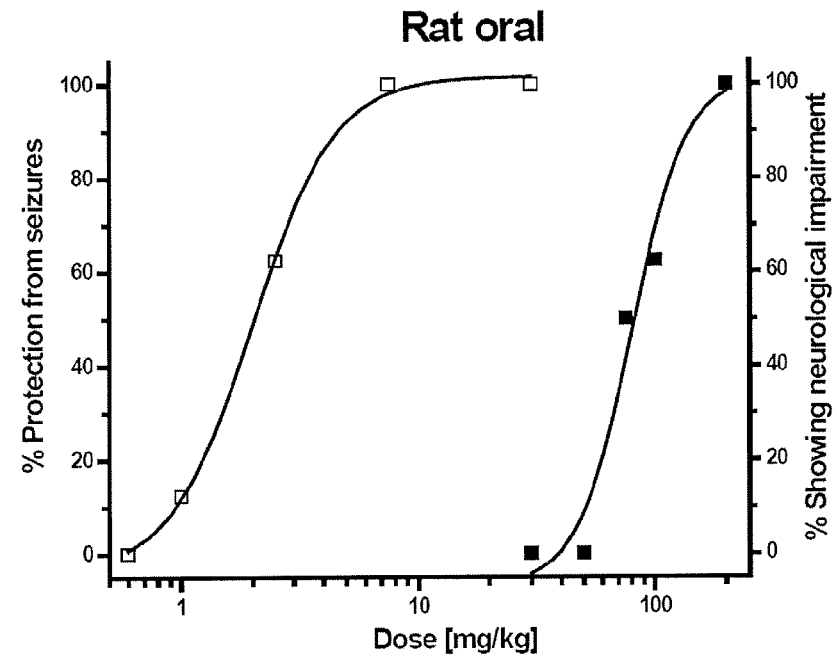

Since this initial screen showed activity in the MES test in two species and an encouraging difference between efficacy and neurotoxicity, SKA-19 was next evaluated quantitatively. When tested for seizure protection in the MES test following i.p. administration at 4 doses (n=8 per dose) SKA-19 was found to have an $ED_{50}$ of 4.8 mg/kg (95% CI, 4.05-5.37) in mice and an $ED_{50}$ of 1.6 mg/kg (95% CI, 1.24-1.94) in rats (FIG. 2). Simultaneously performed toxicity tests for abnormal neurological status revealed a $TD_{50}$ for affecting the ability of mice to stay on the rotorod of 29.8 mg/kg (95% CI, 25.35-35.98, 6 doses, n=8 per dose). At 100 mg/kg two out of 8 mice died. The neurological status of rats as determined by their ability to perform normally in three simple neurological tests was affected with a $TD_{50}$ of 14.33 mg/kg (95% CI, 10.72-17.9, 5 doses, n=8 per dose). Taken together, these tests rendered a therapeutic ($TD_{50}/ED_{50}$) or protective index (PI) of 6.2 for mice and of 8.9 for rats following intraperitoneal application of SKA-19. The protective index was found to be considerably higher (~33) following oral application in rats (FIG. 2) which rendered an $ED_{50}$ in the MES test of 2.33 mg/kg (95% CI, 1.3-3.39, 4 doses, n=8 per dose) and a $TD_{50}$ of 77.38 mg/kg (95% CI, 62.55-91.01). No deaths occurred in rats at higher doses.

Interestingly, when we subsequently submitted riluzole to the ASP, this clinically used drug was found to exhibit a surprisingly high toxicity. In the initial screen, riluzole already affected rotorod performance and righting reflexes in 8 out of 8 mice at 30 mg/kg and killed 8 out of 8 mice at 100 mg/kg following intraperitoneal application. In rats, 30 mg/kg i.p. completely protected animals from MES induced seizures but also killed one animal and induced neurological deficits in 4 out of 4 animals. Subsequent quantitative evaluation of riluzole in the mouse MES test rendered an $ED_{50}$ of 4.07 mg/kg (95% CI, 3.28-4.85, 6 doses, n=8 per dose) and a $TD_{50}$ of 17.27 mg/kg (95% CI, 15.58-19.14, 6 doses, n=8). Riluzole was further looked at after oral application in rats, where it was found to have an $ED_{50}$ of 2.64 mg/kg (95% CI, 1.81-3.75, 4 doses, n=8 per dose) and a $TD_{50}$ of 21.44 mg/kg (95% CI, 14.59-27.85). Overall, riluzole thus appeared to be nearly as potent as SKA-19 but more toxic with a PI of only 4.2 following i.p. administration in mice and a PI of 8 after oral application in rats. Riluzole was also much better tolerated in mice after oral application ($TD_{50}$ 55.26 mg/kg; 95% CI 46.35-65.98). Based on this much better oral tolerability and the MES experiments (shown in FIG. 5) showing no significant difference in the toxicity of SKA-19 and riluzole when administered as solutions, we believe that there is no substantial difference in the relative toxicity of the 2 compounds and that the differences observed in the initial screen were probably caused by quicker absorption of riluzole out of the methylcellulose suspension used by the ASP. In keeping with this notion, riluzole typically reached its maximal effect more quickly (0.25 or 0.5 h) than SKA-19. Like SKA-19, riluzole showed no significant activity in the scMET test.

SKA-19 is Active in the 6-Hz Seizure Test and in Hippocampal Kindled Rats.

Since the combination of the MES and scMET test is known to sometimes miss novel AEDs effective for therapy-resistant partial seizures like levetiracetam, SKA-19 was also examined in the 6-Hz psychomotor seizure test in mice. The 6-Hz test is a limbic seizure model induced by a low frequency, long-duration stimulus delivered by a corneal electrode (White et al., 2002). It produces an initial stun followed by vibrissae chomping, forelimb clonus and a Straub tail. In an initial screen SKA-19 exhibited full protection (4 out of 4 animals) 2 hours after i.p. administration of 10 mg/kg and partial protection at all other tested time points. Subsequent quantitative testing of multiple doses at the 2 h time point (FIG. 3) rendered an $ED_{50}$ of 12.19 mg/kg (95% CI, 8.2-17.45, n=8 per dose). A second set of 6-Hz experiments was performed with a higher current intensity of 44 mA at which the 6-Hz test becomes more discriminatory and has been suggested as a model for therapy-resistant seizures (Barton et al., 2001). At this higher current intensity SKA-19 was found to exhibit an $ED_{50}$ of 28.15 mg/kg (95% CI, 18.14-46.78, n=8 per dose). However, it should be noted when judging the 6-Hz test that SKA-19 was tested at 5, 10, 20, 40 and 60 mg/kg and that the 40 and 60 mg/kg dose are above the $TD_{50}$ (29.73 mg/kg) for affecting mouse rotorod performance. Orally administered riluzole exhibited similar efficacy in the 6-Hz test, but reached its peak effect earlier than SKA-19 ($ED_{50}$ 10.1 mg/kg with a current intensity of 32 mA, and 11.54 mg/kg with a current intensity of 44 mA at the 0.5-h and 1-h time points, respectively).

Figure 3A:
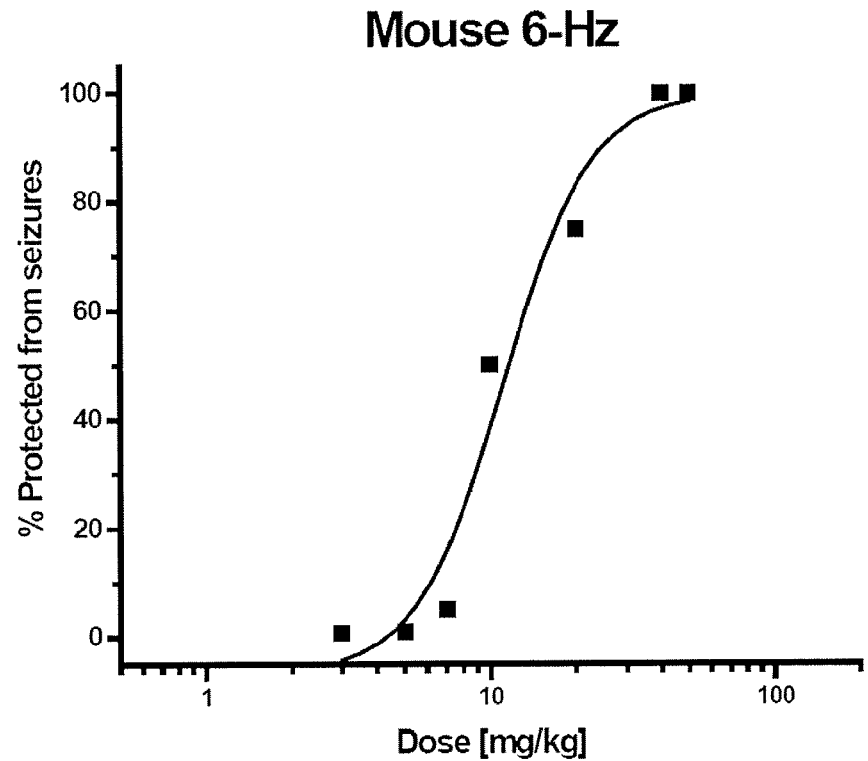
FIG. 3A-FIG. 3C show that SKA-19 exhibits efficacy in the 6-Hz seizure test in mice and in hippocampal kindled rats.
Figure 3B:
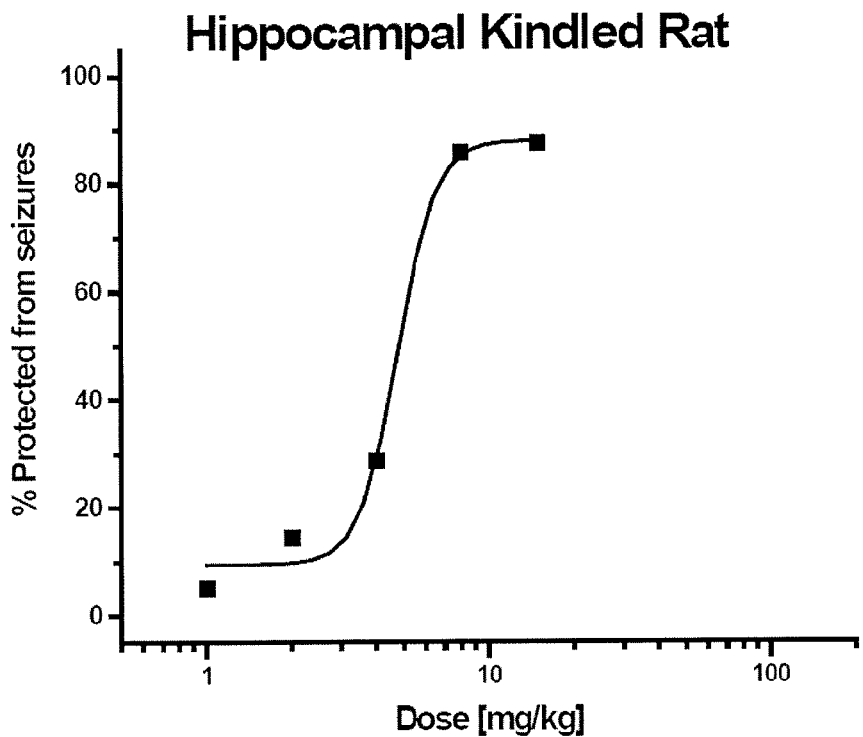

SKA-19 was next evaluated in hippocampal kindled rats, a model that can predict efficacy of an AED for treating complex partial seizures and preventing seizure spread from a focus (Bialer et al., 2010; White et al., 2002). In a preliminary experiment with two fully kindled rats SKA-19 at 30 mg/kg i.p. reduced the predrug seizure score from 4-5 to 0 and completely suppressed the afterdischarge duration (ADD). As shown in FIG. 3, a quantitative test of increasing doses in kindled rats determined an $ED_{50}$ of 5.47 mg/kg (95% CI, 2.92-8.92, n=8 per dose) with no evidence of toxicity at the highest dose (15 mg/kg) in these "seizure experienced animals" despite the fact that this dose was similar to the previously determined $TD_{50}$ in normal, not kindled rats (see FIG. 2B). In lamotrigine resistant amygdala kindled rats, SKA-19 only exhibited partial protection with 2 out of 8 rats protected at 6 mg/kg and 3 out of 7 fully kindled rats protected at 50 mg/kg.

Figure 3C:
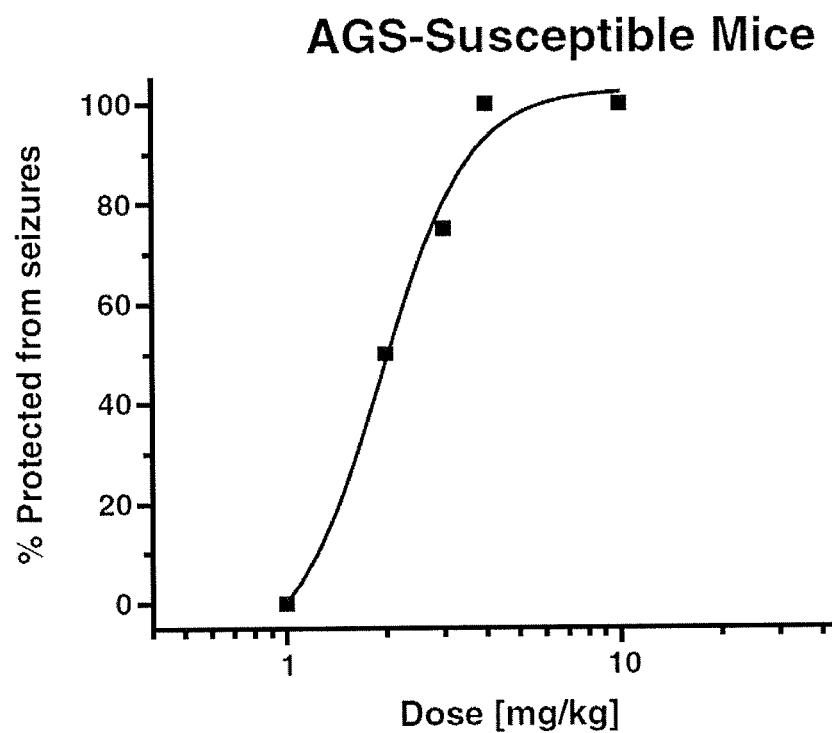

SKA-19 was further evaluated in the Frings AGS-susceptible mouse model (Frings et al., 1953). Frings AGS-susceptible mice exhibit sound-induced seizures, which manifest as wild running, loss of righting reflex, tonic flexion, and tonic extension in response to high-intensity sound stimulation such as a 20-s 110 decibels sound. While the model typically does not differentiate well between different anticonvulsants and is not useful for identifying compounds effective in difficult-to-treat partial seizures (Bialer et al., 2004), its utility rests in its usefulness at predicting potential efficacy against hereditary epilepsy. As shown in FIG. 3C, SKA-19 protected Frings AGS-susceptible mice from sound induced seizures with an $ED_{50}$ of 2.15 mg/kg (95% CI 1.52-2.65; n=8 per dose).

SKA-19 does not Affect Seizure Threshold in the IV Metrazole Test.

Since some anticonvulsants can paradoxically lower seizure threshold and act as "proconvulsants" under certain circumstances, SKA-19 was evaluate in the i.v. Metrazole test, which measures whether a compound lowers or increases the time to the first twitch or to clonus during a continuous i.v. infusion of Metrazole. Vehicle or SKA-19 at 5 and 30 mg/kg, doses corresponding to the mouse MES $ED_{50}$ and the mouse $TD_{50}$ (FIG. 2), were administered i.p. to mice (n=10 per group). The lower dose did not change the time or metrazole dose to the first twitch or clonus, while the higher dose increased both slightly (Metrazole dose to first twitch: vehicle 28.0±0.96 mg/kg, SKA-19 31.6±1.0 mg/kg, p=0.008; Metrazole dose to first clonus: vehicle 30.6±1.19 mg/kg, SKA-19 37.2±1.25 mg/kg, p=0.000). This slight elevation in threshold at 30 m/kg is in keeping with SKA-19 having anti-seizure activity and demonstrates that SKA-19 is not proconvulsant.

Pharmacokinetics of SKA-19.

Figure 4A:
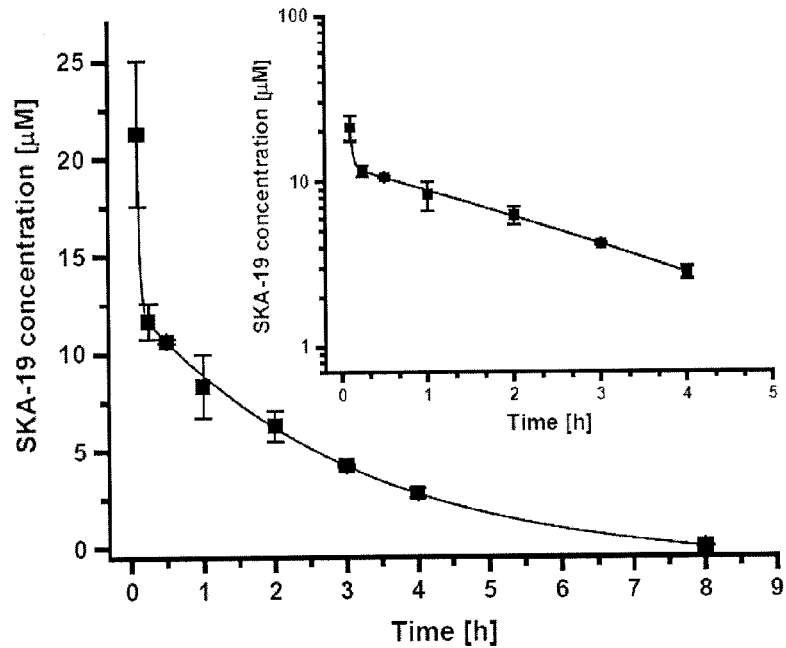
FIG. 4A-FIG. 4D show the pharmacokinetics of SKA-19.

The anticonvulsant testing at the ASP had shown that SKA-19 must have a relatively good bioavailability since it was effective following both oral and intraperitoneal application as a suspension in 0.5% methylcellulose. Activity typically peaked between 1-2 hours and lasted 4 hours, sometimes even longer as in the case of the sedation and neurological impairment which were observable for up to 24 h following administration of 200 mg/kg SKA-19 in the toxicity studies. This prolonged effect suggested a half-life somewhere between 1 and 3 hours. In order to determine the pharmacokinetic properties of SKA-19 we established an UPLC/MS assay based on a HPLC/MS assay we had previously published for the benzothiazole SKA-31 (Sankaranarayanan et al., 2009) and determined total SKA-19 plasma concentrations in rats following i.v., i.p. and oral application as a solution. Following i.v. administration at 10 mg/kg (n=3), SKA-19 plasma concentrations fell bi-exponentially reflecting a 2-compartment model with very rapid distribution from blood into tissue followed by elimination with a half-life of 2.2 h (FIG. 4A). SKA-19 administration in methylcellulose suspension as used by the ASP resulted in a slightly lower plasma concentrations and an oral availability of about 50%.

Figure 4B:
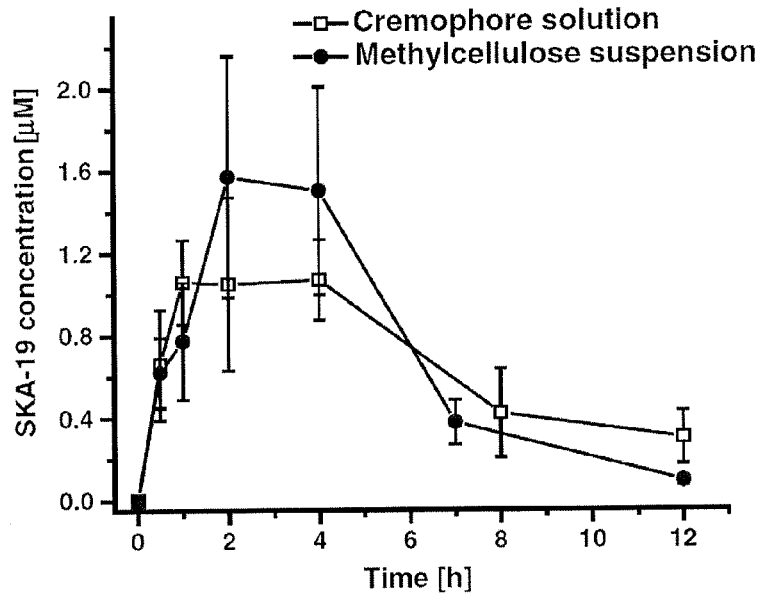
Figure 4C:
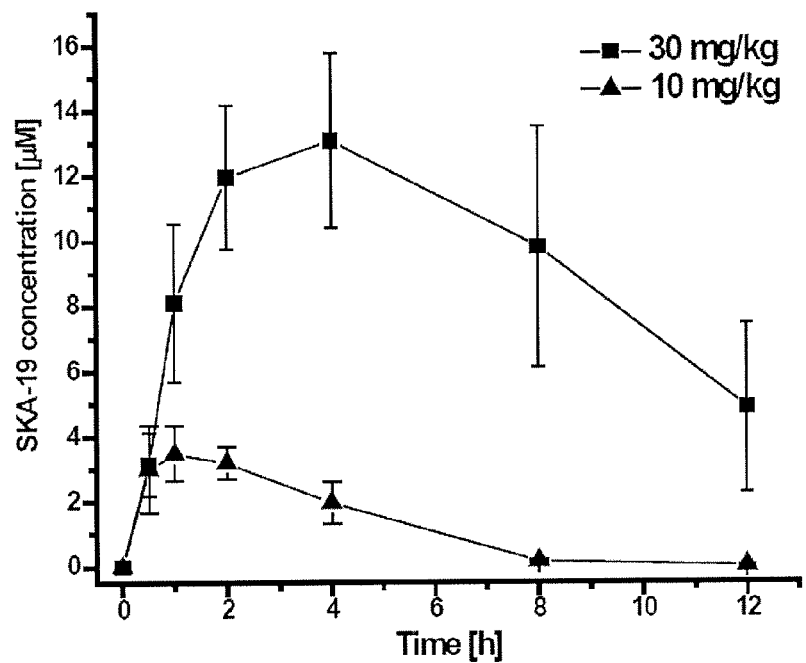

Following oral administration of a solution of 10 mg/kg, SKA-19 plasma concentrations stayed around 1 µM for 5 h and then fell to 0.4 µM at 8 h (FIG. 4B). Gavage of SKA-19 as a suspension in methylcellulose as used by the ASP resulted in a very similar plasma concentrations (FIG. 4B). The plasma peak was slightly delayed and the peak concentration slightly higher (1.6±0.6 µM); however, the overall exposure level was not significantly different. Oral availability was found to be roughly 30% in both vehicles.

We further injected SKA-19 i.p. at concentrations of 10 and 30 mg/kg. In keeping with the high total plasma concentrations measured at 2 hours (11.96±2.21 µM, n=3) and 4 hours (13.09±2.67 µM), rats receiving 30 mg/kg showed prolonged sedation but recovered without weight loss at 24 h.

Figure 4D:
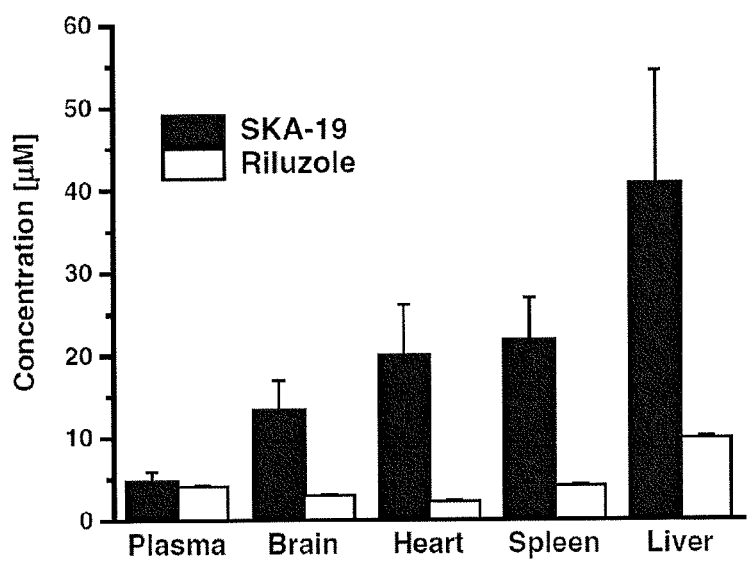

Tissue concentration determinations performed 2 h after i.p. application of 10 mg/kg revealed that SKA-19 is very effective at penetrating into tissues such as brain, heart, spleen, and liver (FIG. 4D). A direct comparison with the same dose of riluzole (10 mg/kg i.p.), which resulted in very similar plasma concentrations at 2 h (4.6±1.3 µM for SKA-19 and 4.1±0.2 µM for riluzole), showed that SKA-19 reached roughly 3-fold higher brain than plasma concentrations, while riluzole exhibited a brain plasma ratio of 1:1 in our hands (FIG. 4D). We further determined the plasma protein binding of SKA-19 and found 82-89% bound with rat plasma.

Direct Comparison of Riluzole and SKA-19 in MES Seizure Test.

Figure 5A:
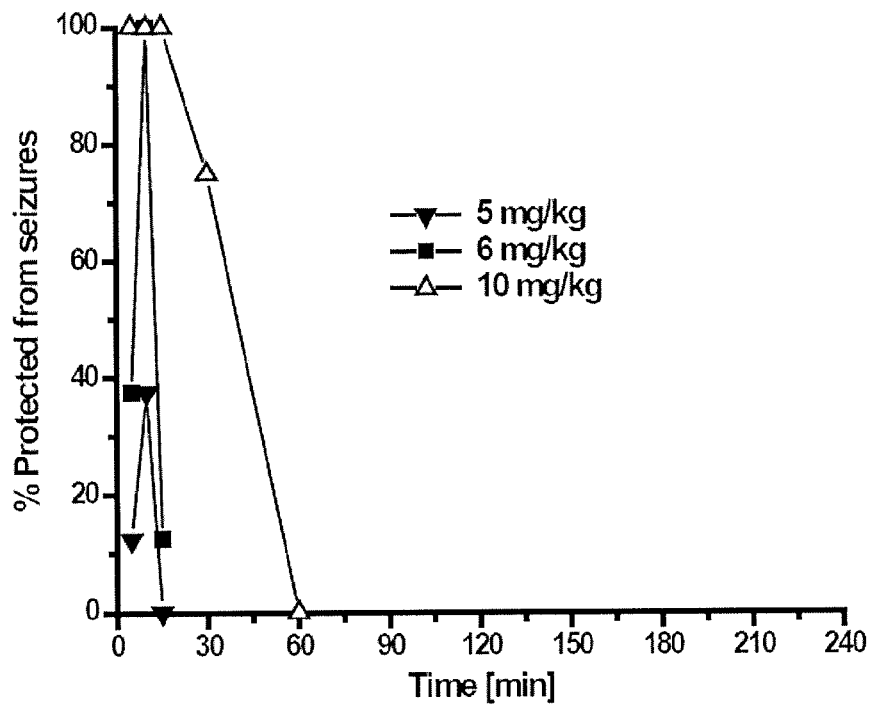
FIG. 5A shows the time course of seizure protection in the mouse MES test following i.p. administration of riluzole as a solution (n=8 per time point).
Figure 5B:
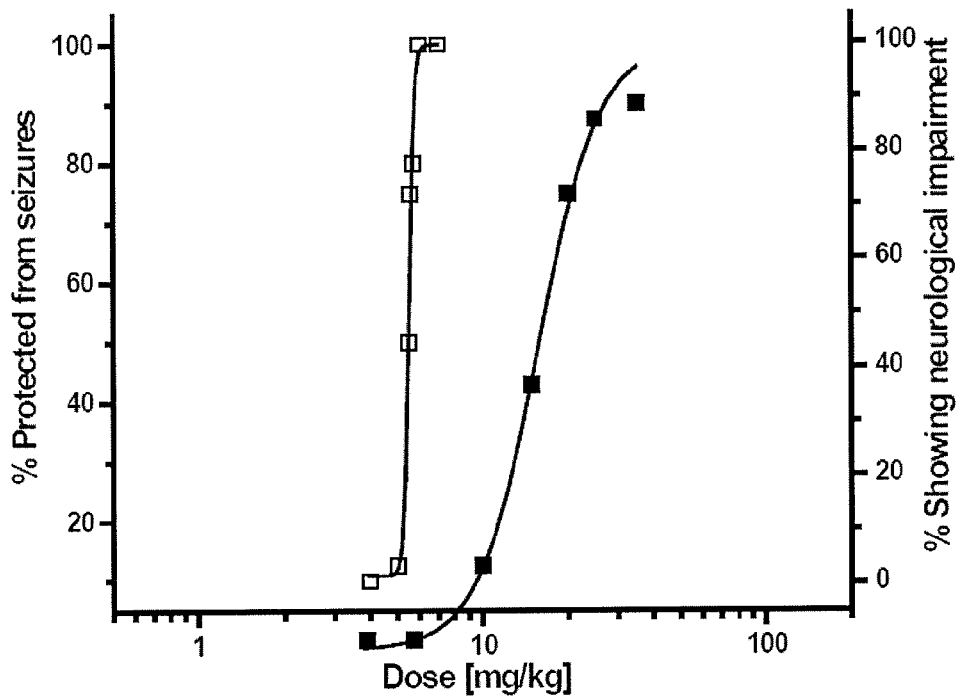
FIG. 5B shows the dose-response curves for seizure protection in the MES test (open squares) and neurological impairment (filled squares) following i.p. administration of increasing riluzole doses in mice (n=8 per dose, 10 min time point). ED50 5.37 mg/kg (95% CI, 5.17-5.57, TD50 15.77 mg/kg (95% CI, 11.94-20.83), PI 2.9.
Figure 5C:
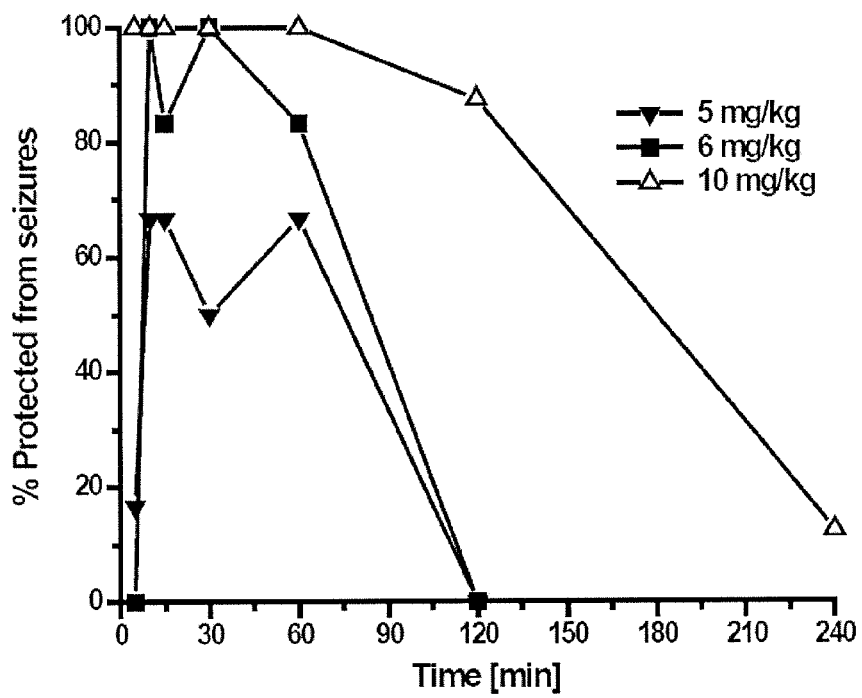
FIG. 5C shows the time course of seizure protection in the mouse MES test following i.p. administration of SKA-19 as a solution (n=6-8 per time point).
Figure 5D:
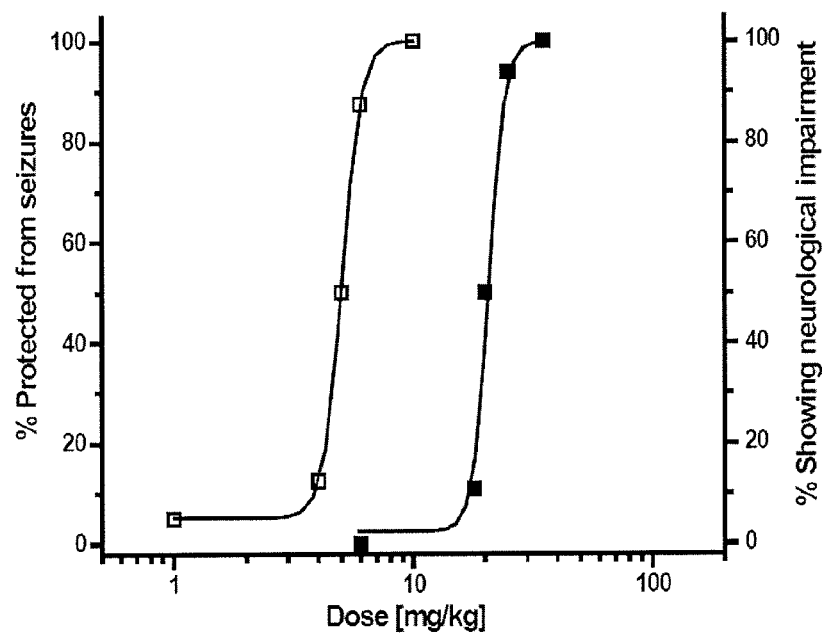
FIG. 5D shows the dose-response curves for seizure protection in the MES test (open squares) and neurological impairment (filled squares) following i.p. administration of increasing SKA-19 doses in mice (n=6-8 per dose, 10 min time point). ED50 4.93 mg/kg (95% CI, 4.15-5.86, TD50 16.08 mg/kg (95% CI, 13.06-19.02), PI 3.2.

In order to directly compare SKA-19 and riluzole we next performed a set of MES experiments in mice. SKA-19 and riluzole were administered i.p. in a volume of 10 ml/kg to assure quick and efficient absorption. Protection from seizures induced by corneal electrodes was seen as early as 5 min after application of both compounds (FIG. 5). However, riluzole only provided a relatively short-lived protection and even 10 mg/kg was not protective for longer than 45 min (FIG. 5A). SKA-19 in contrast provided full protection for 2.5 h at the 10 mg/kg dose and significant seizure protection at 5 and 6 mg/kg for at least 90 min (FIG. 5C). Quantitative testing at the 10 min time point rendered an $ED_{50}$ of 4.93 mg/kg (95% CI, 4.15-5.86, n=6-8 per dose) and a $TD_{50}$ of 16.08 (95% CI, 13.06-19.02) for SKA-19, and very similar $ED_{50}$ and $TD_{50}$ values for riluzole (FIGS. 5B and 5D).

The protective index ($TD_{50}/ED_{50}$) for SKA-19 in these experiments was lower (PI 3.2) than with the suspension application but the $ED_{50}$ was identical to the mouse $ED_{50}$ determined in the MES test by the ASP at 2 hours suggesting that the severity of the neurological impairment induced by SKA-19 depends partially on how quickly brain concentrations rise. The brain is a well perfused organ and following i.p. application of SKA-19 in a high volume, brain concentrations are likely to rise much more quickly than after i.p. administration of a suspension. In keeping with this interpretation, SKA-19 displayed the lowest toxicity following oral application. In this case the PI was found to be 33 (FIG. 2C), probably because brain concentrations rose more slowly in parallel with the slower rise in plasma concentrations observed after oral dosing.

SKA-19 Blocks Sodium Channels and Activates KCa2 Channels.

Figure 5E:
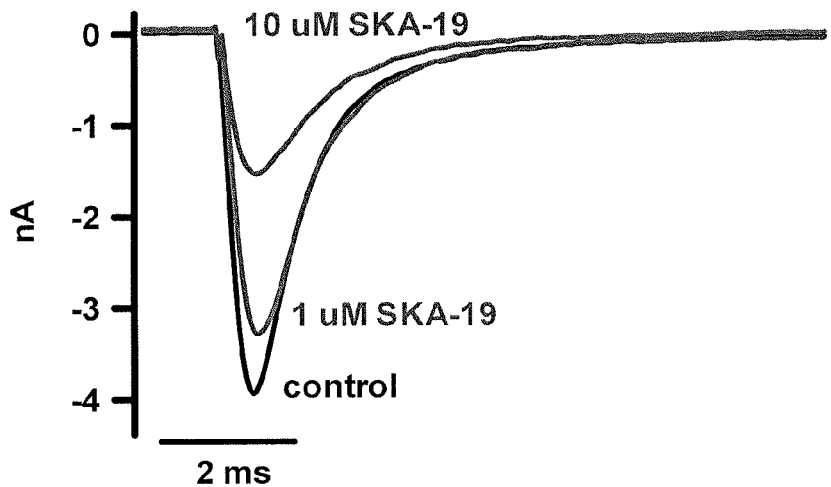
FIG. 5E-FIG. 5J show that SKA-19 is a state- and use-dependent inhibitor of $Nav_{1.2}$ currents in N1E-115 neuroblastoma cells.
Figure 5F:
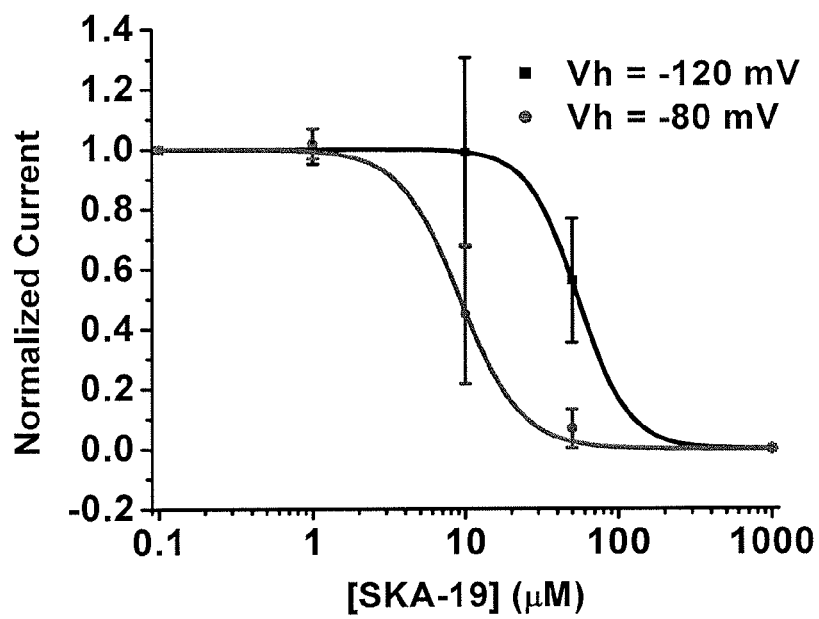
Figure 5G:
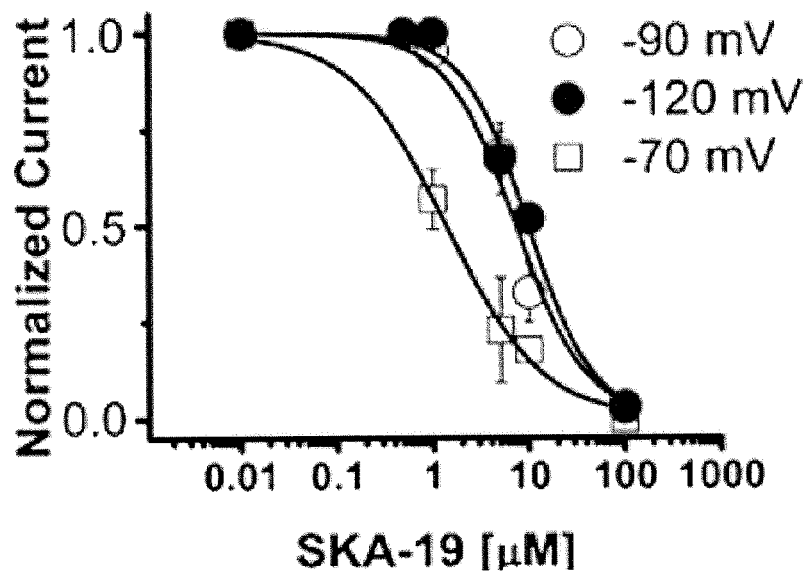
Figure 5H:
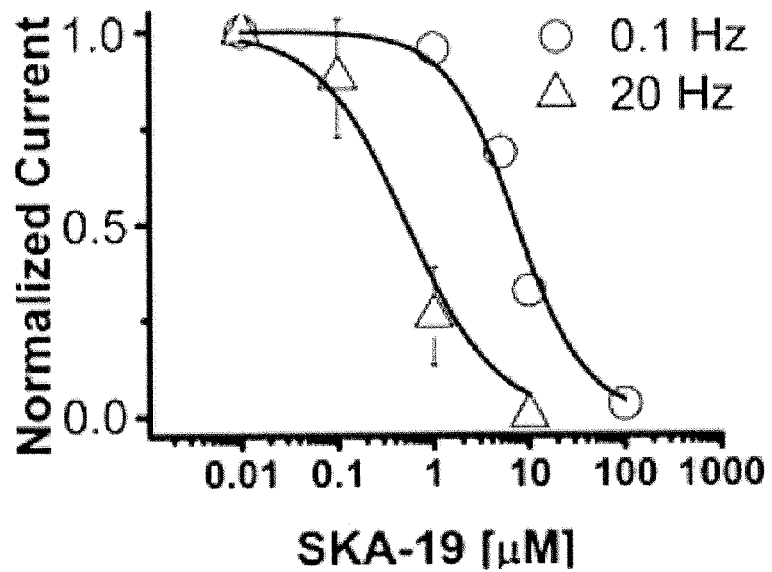
Figure 5I:
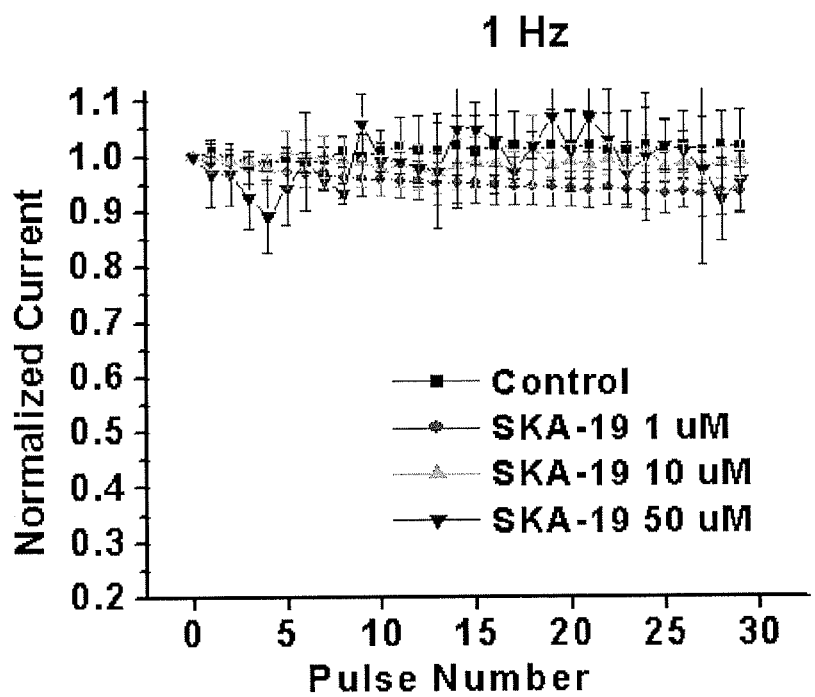
Figure 5J:
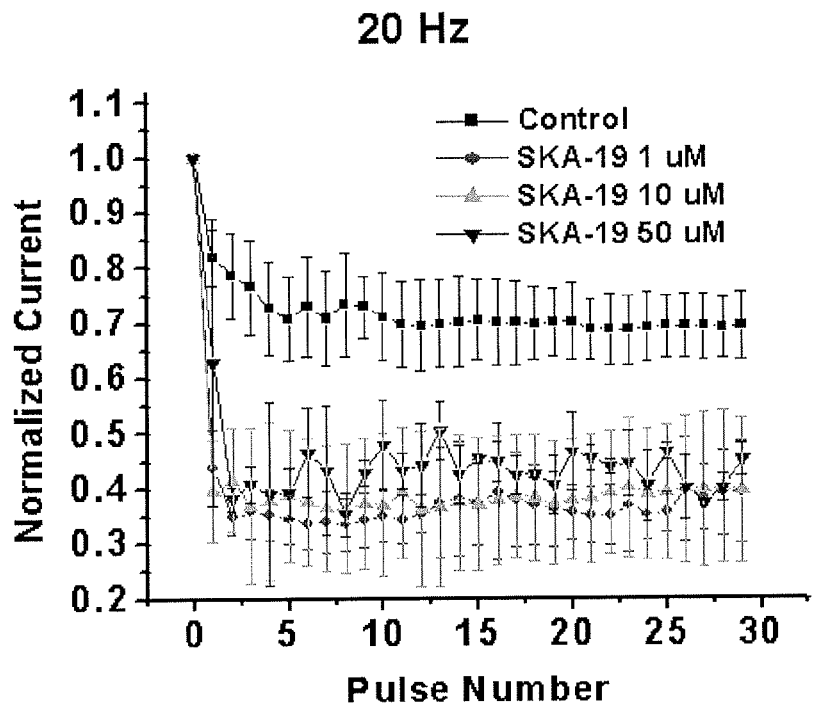
Figure 5K:
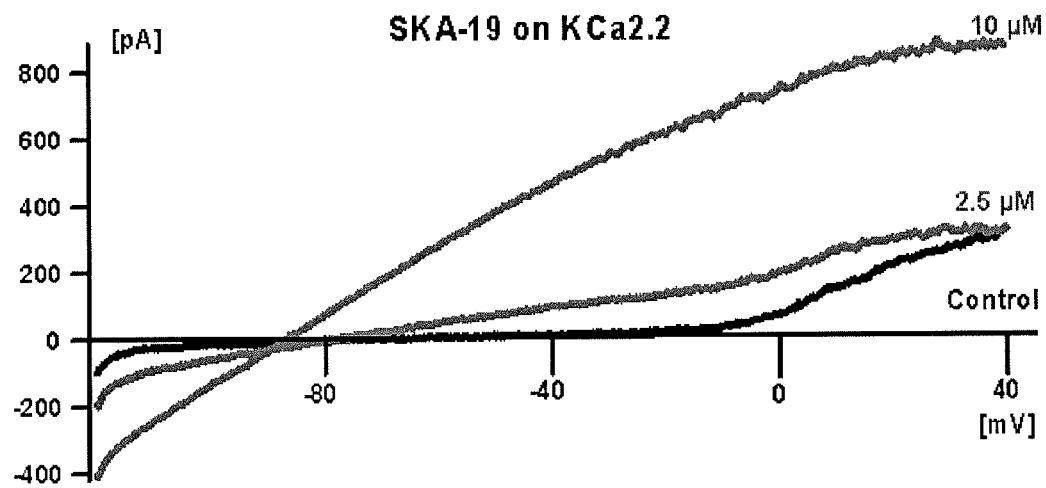
FIG. 5K and FIG. 5L show that SKA-19 activates human KCa2.2 (SK2) and human KCa2.3 (SK3) currents at micromolar concentrations. Recordings were performed on HEK-293 cells stably expressing the KCa2 channel clones and with 250 nM of free $Ca^{2+}$ in the internal solution.
Figure 5L:
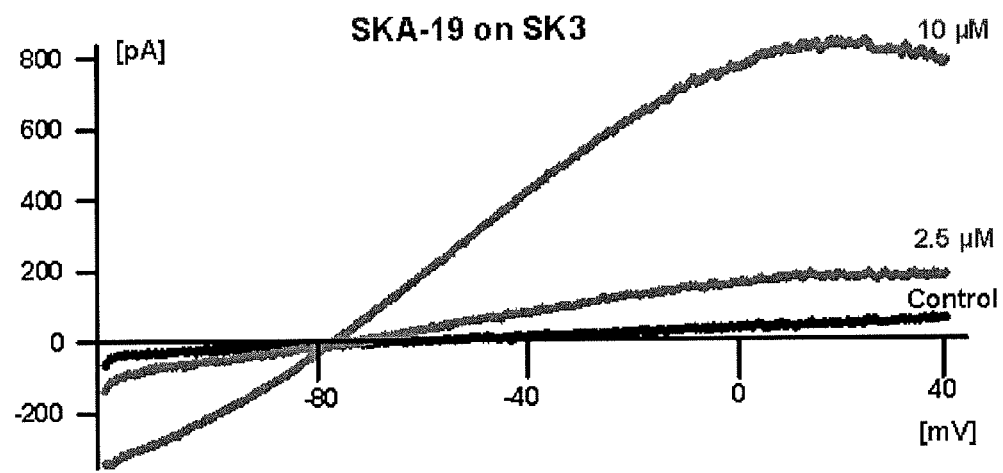

SKA-19 blocks Nav1.2 currents in N1E-115 neuroblastoma cells in a use-dependent and frequency dependent fashion (FIGS. 5E-5H). SKA-19 is more potent at higher pulse frequencies and at more depolarized membrane potentials. SKA-19 activates human KCa2.2 (SK2) and human KCa2.3 (SK3) currents at micromolar concentrations (FIGS. 5K and 5L). Recordings were performed on HEK cells stably expressing the KCa2 channel clones and with 250 nM of free $Ca^{2+}$ in the internal solution.

SKA-19 Shows Efficacy in Pain Models.

Figure 7A:
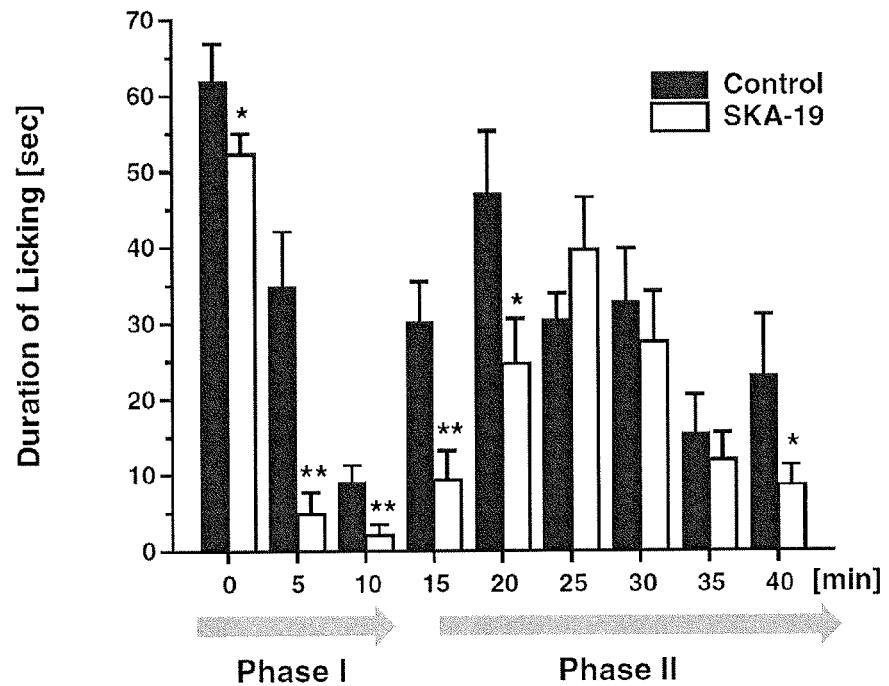
FIG. 7A and FIG. 7B show the effects of SKA-19 administration in a mouse pain model.
Figure 7B:
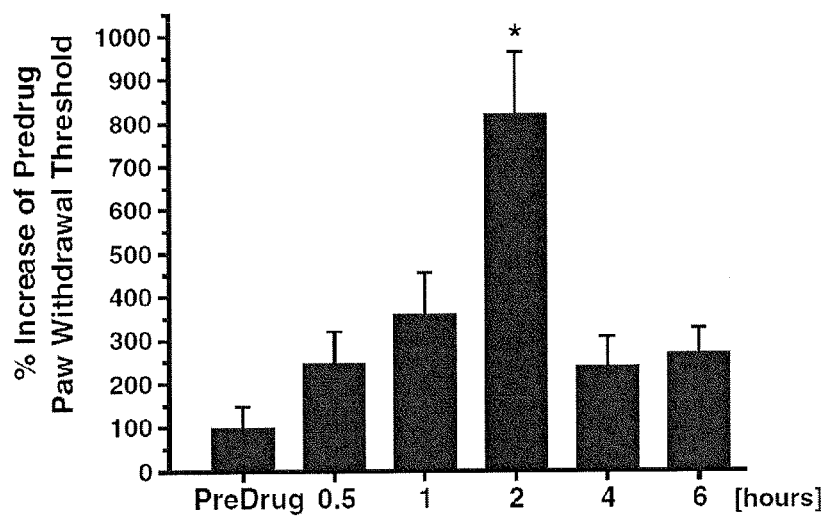

Intraplantar injection of a dilute formalin solution (0.5%) into the hind paw induces a biphasic pain response in mice. Immediately following the injection the mouse intensely lifts, licks, flicks the paw for approximately 5-10 min. This first phase (Phase 1) is thought to result from a direct activation of primary afferent neurons and has recently been shown to be largely caused by direct stimulation of TRPA1 (McNamara et al., 2007). After a brief latent period where there is little behavioral activity, a more prolonged Phase II of about 30-60 min of activity then ensues, which is characterized by sensitization of CNS neurons in the dorsal horn, continuing afferent input and inflammation. SKA-19 administration at 5 mg/kg 2 hours prior to formalin injection significantly decreased nociceptive behavior measured as the amount of time animals spent licking the affected hind paw in a two minute period recorded at 5 minute intervals in Phase I and the early Phase II (FIG. 7). Quantification by determining the area under curve showed a 54.5% reduction of the total paw licking in Phase I (n=8 per group, p<0.05) and a 31.3% reduction of paw licking in Phase II (p<0.05), which the individual time points showing significant reductions up to 20 min.

SKA-19 was further evaluated for its ability to raise allodynic threshold in a Von Frey test following partial sciatic nerve ligation in rats. The threshold for foot withdrawal in response to a series of calibrated Von Frey fibers was determined in rats 7 days after recovery from nerve ligation surgery (n=8). Subsequent SKA-19 administration at 5 m/kg significantly increased the withdrawal threshold from at the 2 hour time point.

Mechanism of action studies showed that SKA-19 suppresses $Ca^{2+}$ oscillations in cultured hippocampal neurons induced by picrotoxin and 4-aminopyridine (4-AP) and inhibits voltage-gated $Na^+$ channels as well as activates KCa2 channels at low micromolar concentrations. SKA-19 further reduced the acute pain response in the formalin pain model and sciatic nerve ligation model. Based on these findings we propose that compounds combining KCa2 channel activating and $Na_v$ channels blocking activity exert broad-spectrum anticonvulsant and analgesic effects in a synergistic manner.

SKA-19 Reduces 4-AP and PTX-Induced $Ca^{2+}$ 21 Oscillations in Hippocampal Neurons.

Figure 6A:
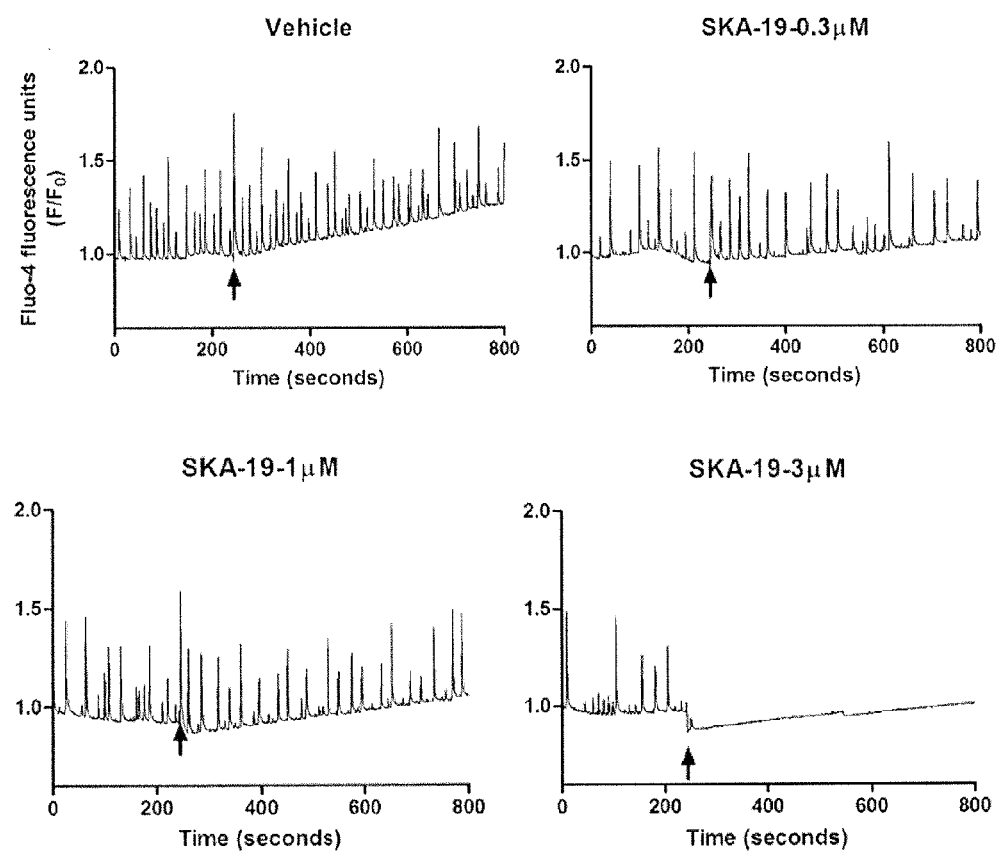
FIG. 6A-FIG. 6C show that increasing concentrations of SKA-19 inhibit spontaneous, 4-AP and picrotoxin induced $Ca^{2+}$ oscillations in cultured 14 DIV hippocampal neurons.
Figure 6B:
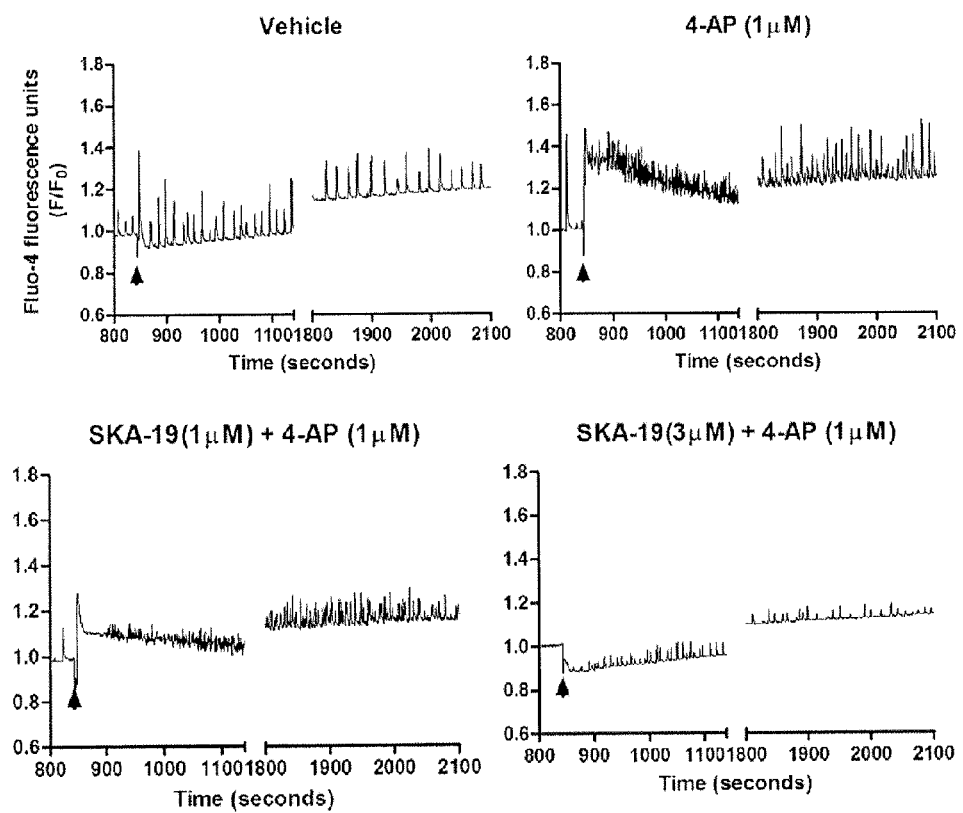
Figure 6C:
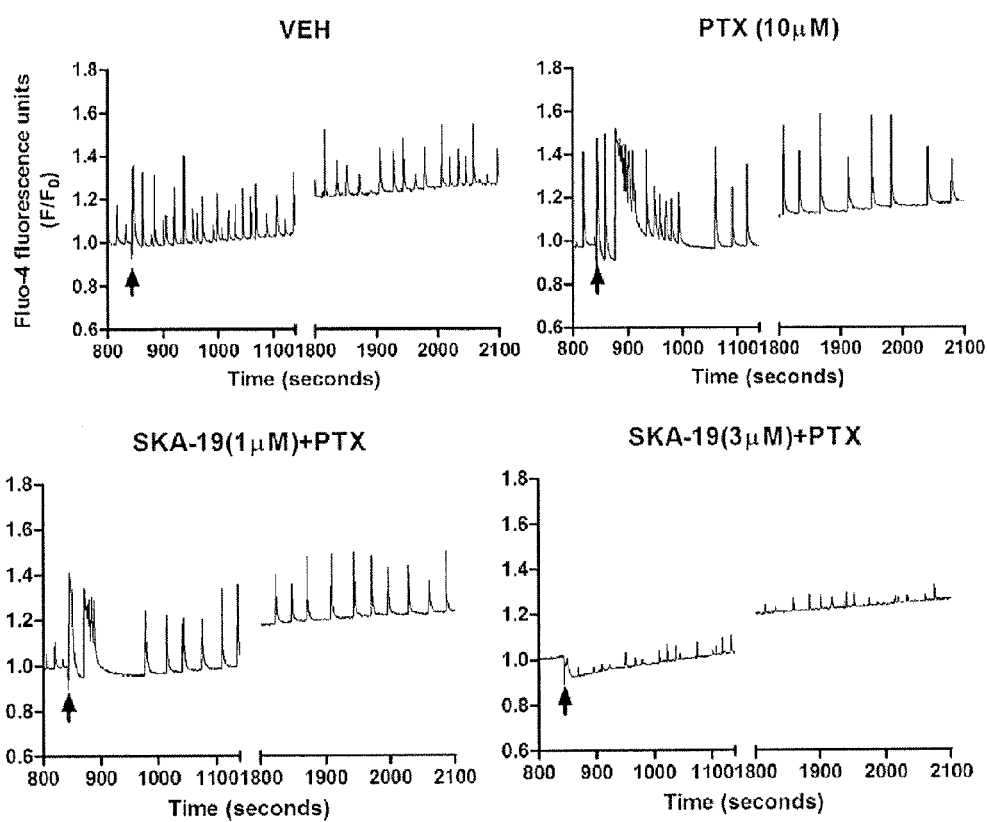

In order to identify the mechanism of action of SKA-19, we started by testing its effect on neuronal $Ca^{2+}$ oscillations. Cultured hippocampal neurons display spontaneous synchronous $Ca^{2+}$ oscillations the frequency and amplitude of which can be monitored in real-time using FLIPR Tetra (Cao et al., 2012). While SKA-19 concentrations of ≤1 did not significantly inhibit spontaneous $Ca^{2+}$ oscillations, SKA-19 concentrations of 3 µM or more completely eliminated spontaneous $Ca^{2+}$ oscillations (FIG. 6A), suggesting that SKA-19 affects neuronal excitability. We next investigated the effect of SKA-19 on $Ca^{2+}$ oscillations induced by the proconvulsant agents 4-AP and picrotoxin (PTX). While the $K^+$ channel blocker 4-AP produced an immediate elevation of neuronal intracellular $Ca^{2+}$ later followed by a drastically increased $Ca^{2+}$ oscillation frequency with lower amplitude (FIG. 6B), the gamma-aminobutyric acid (GABA) receptor A ($GABA_A$) blocker PTX caused a sharper and more transient rise in intracellular $Ca^{2+}$, which was followed by a decrease in the frequency but a rise in the amplitude of $Ca^{2+}$ oscillations (FIG. 6C). SKA-19 potently suppressed both the initial rise and the oscillations induced by both agents, suggesting that it significantly affects neuronal activities driving the $Ca^{2+}$ oscillations induced by 4-AP and PTX in these neuronal networks.

SKA-19 Reduces AP Firing in CA1 Pyramidal Neurons by Inhibiting $Na_v$ Channels and Activating KCa2 Channels.

Figure 8A:
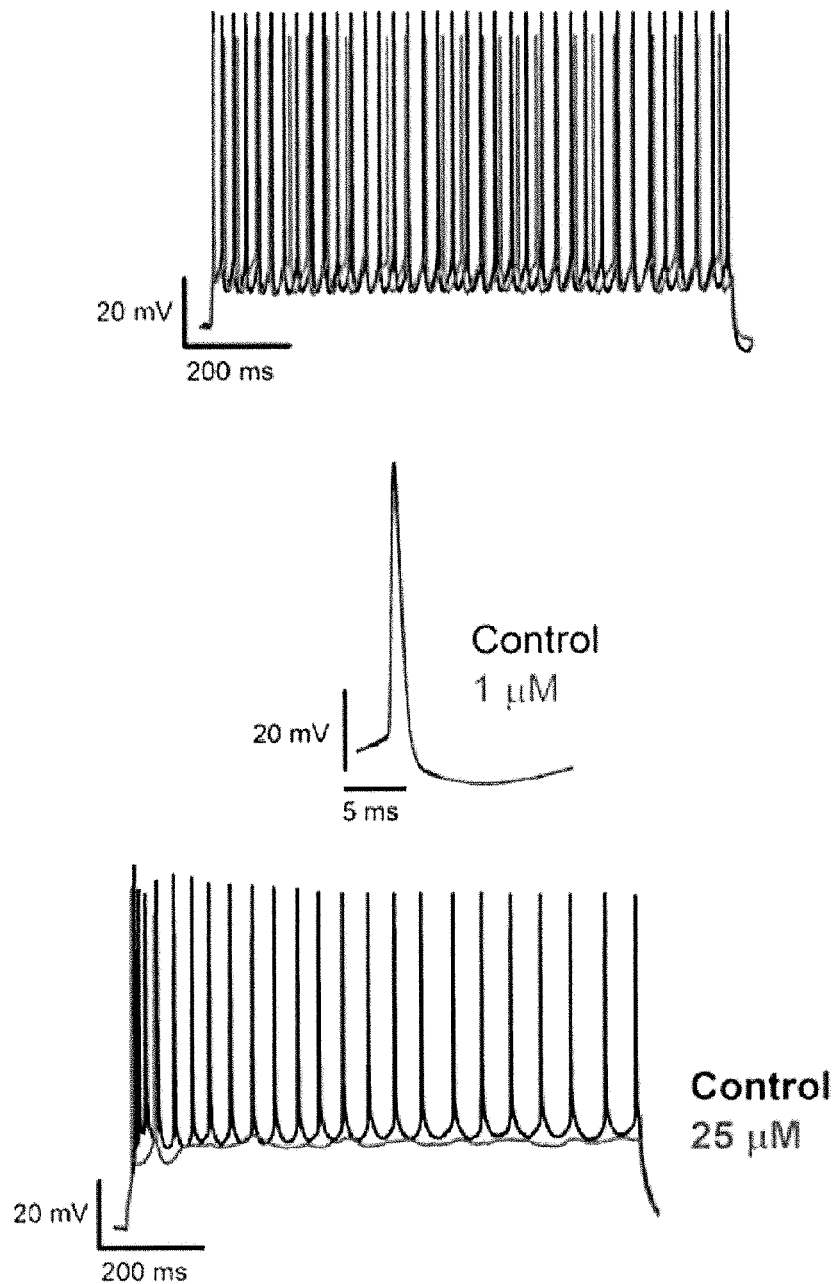
FIG. 8A-FIG. 8D show that 2-amino-6-trifluoromethyl-thio-benzothiazole (SKA-19) reduces action potential (AP) firing of hippocampal pyramidal neurons by activating KCa2 channels and inhibiting voltage-gated Na+ channels (Nav) channels.
Figure 8B:
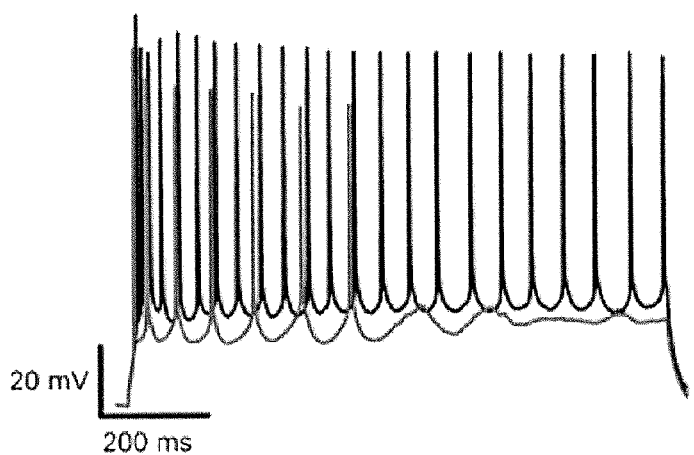
Figure 8B:
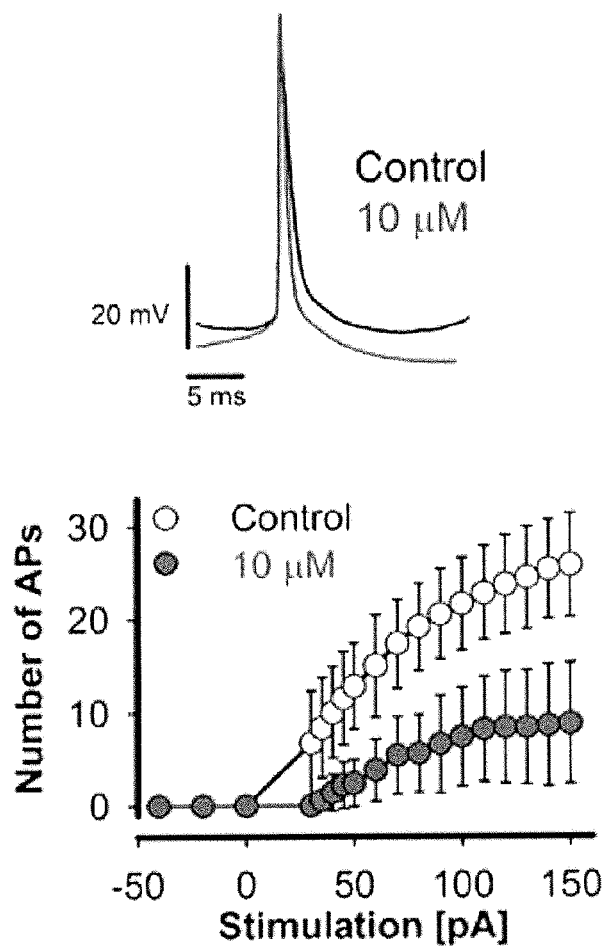
Figure 8C:
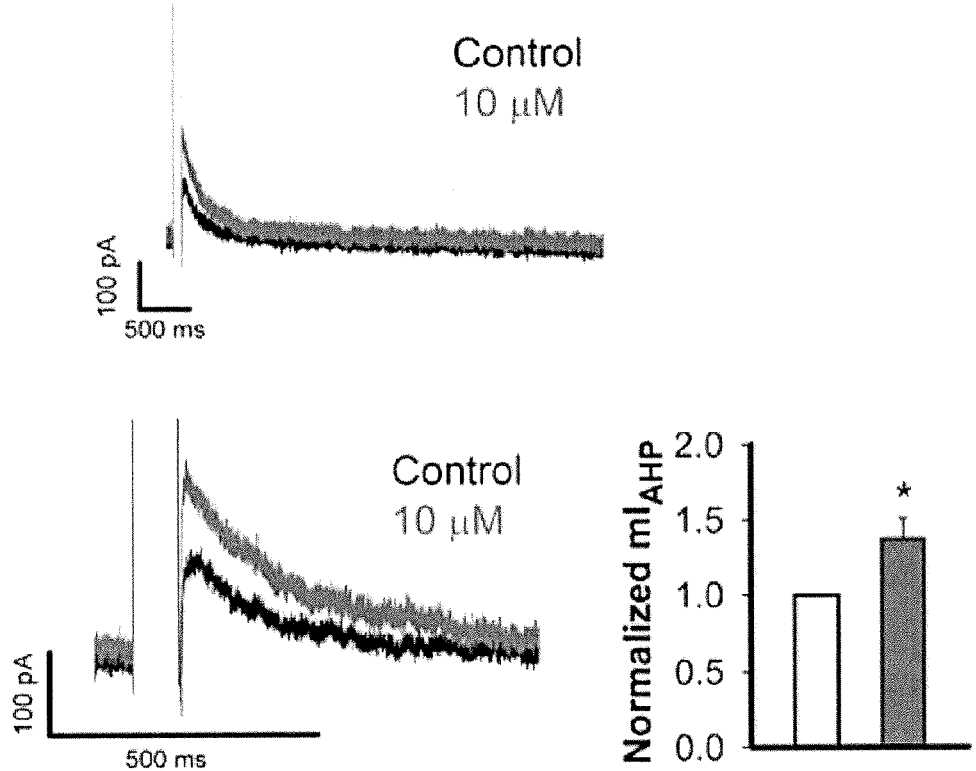
Figure 8D:
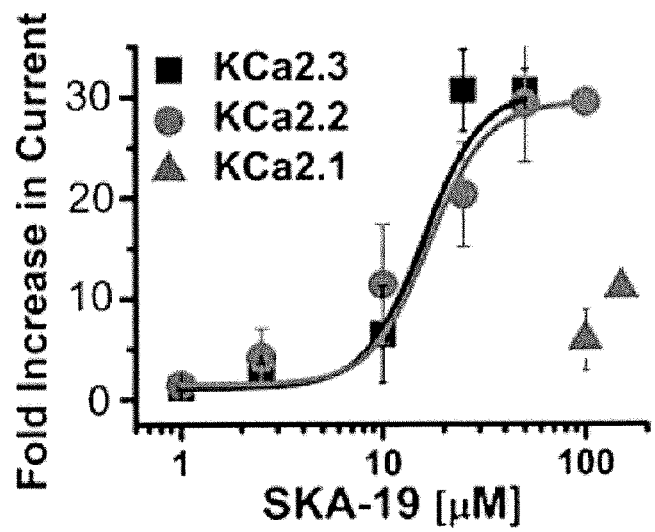

As SKA-19 is a potent anticonvulsant in multiple seizure models and suppresses neuronal $Ca^{2+}$ oscillations, we next tested its effect on firing of CA1 pyramidal neurons in mouse hippocampal slices. Under normal conditions CA1 neurons started firing action potentials (APs) following injection of 30-pA current and subsequently fired APs with increasing frequency at higher current injections. Following a 1-s 150-pA current injection to elicit a series of APs, application of 1 µM SKA-19 slowed down AP firing, while 25 µM completely suppressed it (FIG. 8A). The intermediate concentration of 10 µM of SKA-19 reduced the number of spikes at all injected current levels by roughly 50% (FIG. 8B). A close inspection of individual APs revealed that exposure to 10 µM SKA-19 was associated with an increase in after-hyperpolarization amplitude, suggesting that the effect of SKA-19 is at least partly due to the activation of KCa2 (=SK) channels. To provide support for this conclusion we compared the effect of SKA-19 with the effect of the more specific KCa2 channel activator NS309 (data not shown). At 10 µM, a concentration at which it had previously been shown to exert saturating effects on the medium afterhyperpolarization (mAHP) in CA1 pyramidal neurons in rat hippocampal slices (Pedarzani et al., 2005), NS309 reduced AP firing frequency following 1-s current injections (150 pA) from a holding potential of −65 mV; however, unlike SKA-19 under the same conditions, it did not terminate firing during the ongoing current train, suggesting that SKA-19 has additional effects on other channels than KCa2 channels. To confirm that SKA-19 reduces neuronal firing at least partly by enhancing KCa2 channel activity, we directly measured the mAHP current in the presence or absence of SKA-19 in voltage-clamp experiments. SKA-19 induced a modest but significant increase in the mAHP amplitude compared with control (FIG. 8C). We next tested SKA-19 on KCa2 channels stably expressed in HEK-293 cells. In whole-cell patch-clamp recordings SKA-19 potentiated KCa2.2 (SK2) and KCa2.3 (SK3) currents elicited by 250 nM of free intracellular $Ca^{2+}$ with $EC_{50}$ values of 14 and 15 µM (FIGS. 5K, 5L, 8D; Table 1). Similar to other positive KCa channel gating modulators like SKA-31 and NS309 (Sankaranarayanan et al., 2009), SKA-19 maximally increased KCa2 currents 30-fold at this intracellular $Ca^{2+}$ concentration. Interestingly, SKA-19 displayed selectivity for KCa2.2 and KCa2.3 over KCa2.1, and only showed very weak effects on KCa2.1 currents at concentrations of 100 and 200 µM (FIG. 8D).

Based on its structural similarity to riluzole, its sedating properties at higher concentrations and its pronounced effects on neuronal firing (FIGS. 8A and 8B), we further suspected that SKA-19 would also block $Na_v$ channels and therefore investigated its blocking properties on several sodium channel isoforms. SKA-19 inhibited $Na_v1.1$ and $Na_v1.2$, two of the major neuronal sodium channels, with $IC_{50}$ values of approximately 7.90±0.01 µM (FIGS. 5E, 5G, 5H; Table 1) when cells were held at −90 mV and pulsed with a frequency of 0.1 Hz. Changing the holding potential or the pulse frequency to 20 Hz revealed that inhibition by SKA-19 was highly state- and use-dependent as both manipulations significantly affected the $IC_{50}$ for $Na_v1.2$ by lowering it to 860 or 520 nM, respectively (FIGS. 5E, 5G, 5H). As expected, SKA-19 did not exhibit any selectivity among sodium channel isoforms and also blocked $Na_v1.4$, $Na_v1.5$, and $Na_v1.7$ in the low micromolar range (Table 1). Taken together, SKA-19 therefore seems to be a "dirty" ion channel modulator that exerts its anticonvulsant and analgesic effects through a combination of KCa2 channel-activating and $Na_v$ channel-blocking activity.

TABLE 1

Selectivity of 2-amino-6-trifluoromethylthio-benzothiazole

| Channels | $EC_{50}$ or $IC_{50}$ (µM) | n |
|---|---|---|
| KCa2.1 | >100 | 5 |
| KCa2.2 | 14 ± 5 | 12 |
| KCa2.3 | 15 ± 5 | 14 |
| $Na_v1.1$ | 6.9 ± 4.9 | 5 |
| $Na_v1.2$ | 7.9 ± 0.02 | 3 |
| $Na_v1.3$ | 2.2 ± 1.1 | 6 |
| $Na_v1.4$ | 4.5 ± 2.7 | 7 |
| $Na_v1.5$ | 5.8 ± 2.6 | 3 |
| $K_v2.1$ | 22.3 ± 5.6 | 3 | n number of cells used per experiment

Comparison of Riluzole and SKA-19.

Riluzole [2-amino-6-(trifluoromethoxy)benzothiazole], a drug marketed for the treatment of amyotrophic lateral sclerosis, is well recognized to have anticonvulsant properties, with a spectrum of activity in animal models similar to sodium-channel blocking antiepileptic drugs. Accordingly, among its various cellular actions, riluzole inhibits neuronal voltage-gated sodium channels in a use-dependent manner. More recently riluzole has been found to activate apamin-sensitive small-conductance $Ca^{2+}$-activated KCa2 (SK) channels, which are widely expressed in the nervous system and are responsible for the medium AHP (afterhyperpolarization) that regulates tonic, burst and rhythmic neuronal firing. Riluzole has been used as a template for the design of structurally novel KCa2 activators. Among the KCa2 activators identified by the approach is the sulfur-substituted riluzole analog SKA-19 [2-amino-6-(trifluoromethylthio) benzothiazole], which has KCa2 activating potency comparable to that of riluzole (Sankaranarayanan et al., 2009). SKA-19 was found to have potent anticonvulsant activity in testing conducted by the NINDS Anticonvulsant Screening Program. In the present study, we compared the anticonvulsant activity of riluzole and SKA-19.

The mouse maximal electroshock (MES) and 6 Hz seizure models were used. Motor toxicity was assessed using a modification of the horizontal screen test. ED50 values in the seizure models and TD50 values in the toxicity test were determined by nonlinear fitting of dose-response curves. Stock solutions (5 mg/ml) of riluzole and SKA-19 were prepared in 10% (5 mg/ml) sulfobutylether-β-cyclodextrin sodium salts (Captisol®) in 0.9% saline and 5% CremophorEL/95% PBS respectively and diluted further with saline. Drugs solutions were injected intraperitoneally 10 min prior to administration of the electrical stimulus in a volume of 10 ml/kg body weight.

Riluzole and SKA-19 were both protective in the MES seizure test with ED50 values of 5.37 and 4.93 mg/kg, respectively. In the 6 Hz test, the ED50 values were 16.36 and 22.54 mg/kg, although these values are uncertain because effective doses cause neurological impairment that precluded a reliable assessment of seizure protection. Although the potency of the two compounds was similar when tested at 10 min in the MES test, SKA-19 (10 mg/kg) had a much more prolonged duration of action. Thus, SKA-19 exhibited protective activity for up to 4 h whereas the duration of activity of riluzole was <1 h. The TD50 values of riluzole and SKA-19 following intraperitoneal administration in solution were 15.77 and 16.33 mg/kg, respectively. Riluzole and SKA-19 exhibit equivalent potency in the MES seizure test but SKA-19 appears to have dramatically improved pharmacokinetic properties.

REFERENCES

Adelman J P, Maylie J, Sah P (2012). *Annual review of physiology* 74: 245-269.

Allen D, Nakayama S, Kuroiwa M, Nakano T, Palmateer J, Kosaka Y, et al. (2011). *J Cereb Blood Flow Metab* 31(12): 2302-2312.

Bahia P K, Suzuki R, Benton D C, Jowett A J, Chen M X, Trezise D J, et al. (2005). *J Neurosci* 25(14): 3489-3498.

Barton M E, Klein B D, Wolf H H, White H S (2001). *Epilepsy Res* 47(3): 217-227.

Bialer M, Johannessen S I, Levy R H, Perucca E, Tomson T, White H S (2013). *Epilepsy Res* 103(1): 2-30.

Bialer M, White H S (2010). *Nat Rev Drug Discov* 9(1): 68-82.

Bialer et al. (2004) *Epilepsy Behav.* 5:866-872.

Biervert C, Schroeder B C, Kubisch C, Berkovic S F, Propping P, Jentsch T J, et al. (1998). *Science* 279(5349): 403-406.

Bond C T, Herson P S, Strassmaier T, Hammond R, Stackman R, Maylie J, et al. (2004). *J Neurosci* 24(23): 5301-5306.

Cao et al. *Toxicol Sci* 2012; 130:362372.

Dalby-Brown W, Jessen C, Hougaard C, Jensen M L, Jacobsen T A, Nielsen K S, et al. (2013). *European journal of pharmacology* 709(1-3): 52-63.

Duprat F, Lesage F, Patel A J, Fink M, Romey G, Lazdunski M (2000). *Mol Pharmacol* 57(5): 906-912.

Edgerton J R, Reinhart P H (2003). *The Journal of physiology* 548(Pt 1): 53-69.

Faber E S, Sah P (2007). *Clin Exp Pharmacol Physiol* 34(10): 1077-1083.

Frings H, Frings M. *Science.* 1953; 117:283-284

Gordon P, Corcia P, Meininger V (2013). *Expert opinion on pharmacotherapy.*

Grunnet M, Jespersen T, Angelo K, Frokjaer-Jensen C, Klaerke D A, Olesen S P, et al. (2001). Pharmacological modulation of SK3 channels. *Neuropharmacology* 40(7): 879-887.

Hammond R S, Bond C T, Strassmaier T, Ngo-Anh T J, Adelman J P, Maylie J, et al. (2006). *J Neurosci* 26(6): 1844-1853.

Kasumu A W, Hougaard C, Rode F, Jacobsen T A, Sabatier J M, Eriksen B L, et al. (2012). *Chemistry & biology* 19(10): 1340-1353.

Kobayashi K, Nishizawa Y, Sawada K, Ogura H, Miyabe M (2008). *J Pharmacol Sci* 108(4): 517-528.

Kokate T G, Svensson B E, Rogawski M A (1994). *J Pharmacol Exp Ther* 270(3): 1223-1229.

Lappin S C, Dale T J, Brown J T, Trezise D J, Davies C H (2005). *Brain Res* 1065(1-2): 37-46.

Lin M T, Luj an R, Watanabe M, Adelman J P, Maylie J (2008). *Nat Neurosci* 11(2): 170-177.

McCown T J, Breese G R (1990). *European journal of pharmacology* 187(1): 49-58.

McNamara C R, Mandel-Brehm J, Bautista D M, Siemens J, Deranian K L, Zhao M, et al. (2007). *Proc Natl Acad Sci USA* 104(33): 13525-13530.

Meisler M H, Kearney J A (2005). *The Journal of clinical investigation* 115(8): 2010-2017.

Mizoule J, Meldrum B, Mazadier M, Croucher M, Ollat C, Uzan A, et al. (1985). *Neuropharmacology* 24(8): 767-773.
Mongan L C, Hill M J, Chen M X, Tate S N, Collins S D, Buckby L, et al. (2005). *Neuroscience* 131(1): 161-175.
Mourre C, Fournier C, Soumireu-Mourat B (1997). *Brain research* 778(2): 405-408.
N'Gouemo P, Yasuda R P, Faingold C L (2009). *Brain Res* 1270: 107-111.
Ngo-Anh T J, Bloodgood B L, Lin M, Sabatini B L, Maylie J, Adelman J P (2005). *Nat Neurosci* 8(5): 642-649.
Pedarzani P, McCutcheon J E, Rogge G, Jensen B S, Christophersen P, Hougaard C, et al. (2005). *J Biol Chem* 280(50): 41404-41411.
Pedarzani P, Mosbacher J, Rivard A, Cingolani L A, Oliver D, Stocker M, et al. (2001). *J Biol Chem* 276(13): 9762-9769.
Rigdon G C (2009). Results of Phase I program for ICA-105665, drug candidate for the treatment of epilepsy and neuropathic pain. In: *Antiepileptic Drug Trials X Conference* Coral Gables, Fla.
Roeloffs R, Wickenden A D, Crean C, Werness S, McNaughton-Smith G, Stables J, et al. (2008). *J Pharmacol Exp Ther* 326(3): 818-828.
Rogawski M A (1996). Epilepsy. In: Pullan L, Patel J Neurotherapeutics: *Emerging Strategies* edn. Totowa, N.J.: Humana Press. 193-273.
Sailer C A, Hu H, Kaufmann W A, Trieb M, Schwarzer C, Storm J F, et al. (2002). *J Neurosci* 22(22): 9698-9707.
Sailer C A, Kaufmann W A, Marksteiner J, Knaus H G (2004). *Mol Cell Neurosci* 26(3): 458-469.
Sankaranarayanan A, Raman G, Busch C, Schultz T, Zimin P I, Hoyer J, et al. (2009). *Mol Pharmacol* 75(2): 281-295.
Song J H, Huang C S, Nagata K, Yeh J Z, Narahashi T (1997). *J Pharmacol Exp Ther* 282(2): 707-714.
Stocker M, Krause M, Pedarzani P (1999). *Proc Natl Acad Sci USA* 96(8): 4662-4667.
Stocker M, Pedarzani P (2000). *Mol Cell Neurosci* 15(5): 476-493.
Verma-Ahuja S, Evans M S, Pencek T L (1995). *Epilepsy Res* 22(2): 137-144.
Villalobos C, Shakkottai V G, Chandy K G, Michelhaugh S K, Andrade R (2004). *J Neurosci* 24(14): 3537-3542.
White H S, Woodhead J H, Wilcox K S, Stables J, Kuferberg H, Wolf H H (2002). Discovery and preclinical development of antiepileptic drugs. In: Levy R H, Mattson R H, Meldrum B, Perucca E. *Antiepileptic Drugs*, 5th edn. Philadephia, Pa.: Lippincott Williams & Wilkins. 36-48.
Wulff H, Kolski-Andreaco A, Sankaranarayanan A, Sabatier J M, Shakkottai V (2007). *Current medicinal chemistry* 14(13): 1437-1457.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method for treating a seizure disorder comprising administering to a subject in need thereof a compound according to formula I:

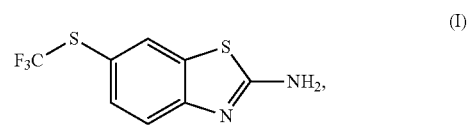 [SMILES: Nc1nc2ccc(SC(F)(F)F)cc2s1]

or a pharmaceutically acceptable salt thereof, wherein the seizure disorder is selected from the group consisting of a limbic seizure, a complex partial seizure, and a chemically-induced seizure.

2. The method of claim 1, wherein the seizure disorder is a limbic seizure.

3. The method of claim 1, wherein the seizure disorder is a complex partial seizure.

4. The method of claim 1, wherein the seizure disorder is a chemically-induced seizure.

5. The method of claim 4, wherein the seizure is induced by exposure of the subject to an organophosphate threat agent.

6. The method of claim 1, wherein the subject is known to be susceptible to the seizure disorder.

7. A method for treating a seizure disorder comprising administering to a subject in need thereof a compound according to formula I:

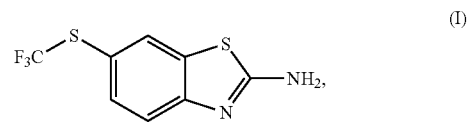 [SMILES: Nc1nc2ccc(SC(F)(F)F)cc2s1]

or a pharmaceutically acceptable salt thereof, wherein
the seizure disorder is susceptible to inhibition of a voltage-gated sodium channel;
the seizure disorder is susceptible to activation of a small-conductance calcium-activated potassium channel; or
the seizure disorder is susceptible to inhibition of a voltage-gated sodium channel and activation of a small-conductance calcium-activated potassium channel.

8. The method of claim 7, wherein the voltage-gated sodium channel is selected from the group consisting of Nav1.1, Nav1.2, and Nav 1.6.

9. The method of claim 7, wherein the small-conductance calcium-activated potassium channel is selected from the group consisting of KCa2.1, KCa2.2, and KCa2.3.

10. The method of claim 1, wherein the compound is administered to the subject while the subject is experiencing an aura.

11. The method of claim 1, wherein the compound is administered to the subject before the seizure onset.

12. The method of claim 1, wherein the compound is administered to the subject during the seizure.

13. The method of claim 1, wherein administration of the compound is sufficient to treat pain in the subject.

14. A method for treating pain comprising administering to a subject in need thereof a compound according to formula I:

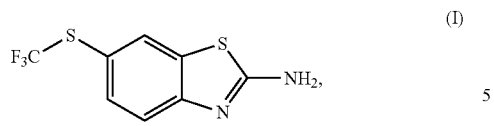

(I)

or a pharmaceutically acceptable salt thereof.

15. The method of claim 1, wherein the compound is administered at a dose below 200 mg of compound per kg of the subject's body weight (200 mg/kg).

16. The method of claim 7, wherein the compound is administered at a dose below 200 mg of compound per kg of the subject's body weight (200 mg/kg).

17. The method of claim 14, wherein the compound is administered at a dose below 200 mg of compound per kg of the subject's body weight (200 mg/kg).

18. The method of claim 1, further comprising administering to the subject one or more agents selected from the group consisting of anticonvulsant agents and analgesic agents.

19. The method of claim 7, further comprising administering to the subject one or more agents selected from the group consisting of anticonvulsant agents and analgesic agents.

20. The method of claim 14, further comprising administering to the subject one or more agents selected from the group consisting of anticonvulsant agents and analgesic agents.

* * * * *

UNITED STATES PATENT AND TRADEMARK OFFICE
CERTIFICATE OF CORRECTION

| | |
|---|---|
| PATENT NO. | : 9,675,591 B2 |
| APPLICATION NO. | : 15/130796 |
| DATED | : June 13, 2017 |
| INVENTOR(S) | : Heike Wulff, Nichole Coleman and David Paul Jenkins |

Page 1 of 1

It is certified that error appears in the above-identified patent and that said Letters Patent is hereby corrected as shown below:

Column 28, Line 50, Claim 8, please delete "Nay 1.6" and insert --Nav1.6--

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*